US006156311A

United States Patent [19]
Strickland et al.

[11] Patent Number: 6,156,311
[45] Date of Patent: Dec. 5, 2000

[54] MODULATORS OF EXPRESSION AND FUNCTION OF LRP IN ALZHEIMER'S DISEASE

[75] Inventors: Dudley K. Strickland, Olney, Md.; Bradley T. Hyman, Swampscott, Mass.; Maria Z. Kounnas, Gaithersburg, Md.; Robert D. Moir, Boston; Rudolph E. Tanzi, Canton, both of Mass.

[73] Assignees: The American National Red Cross, Washington, D.C.; The General Hospital Corporation, Boston, Mass.

[21] Appl. No.: 08/687,668

[22] Filed: Jul. 26, 1996

Related U.S. Application Data

[60] Provisional application No. 60/001,600, Jul. 25, 1995.
[51] Int. Cl.[7] .......................... A61K 39/395; A61K 38/00
[52] U.S. Cl. ..................................... 424/130.1; 424/143.1; 424/152.1; 514/2
[58] Field of Search ............................... 424/143.1, 139.1, 424/130.1, 152.1; 514/8.2, 12, 13, 14, 15, 16, 17, 18, 2; 350/300, 350, 387.1, 388.1, 388.22

[56] References Cited

PUBLICATIONS

The Physiccans' Desk Reference®, 1981 by Litton Industries 35th edition p. 1933.
Gotfries etal, European Neuropsychopharmacology 1:1–5, 1990.
McGeer etal, Neurology, 42:447–449, Feb. 1992.
Rovner, The Washington Post, Oct. 5, 1993.
Winker, JAMA, 271(13):1023–1024, 1994.
Barinagu, Science, 264:772–774, 1994.
Shrine, J., BioWorld Today, 5(123):1.
Horn, I.R. et al., "Recombinant fragments of the second cluster of complement–type repeats of LRP mediate high affinity binding of different ligands as determined by surface plasmon resonance," *Fibrinolysis* 10(Suppl. 3):21 (Abstract 61) (Jun. 1996).
Kounnas, M.Z. et al., "LDL Receptor–Related Protein, a Multifunctional ApoE Receptor, Binds Secreted β–Amyloid Precursor Protein and Mediates Its Degradation," *Cell* 82:331–340 (Jul. 1995).
Kounnas, M.Z. et al., "LDL Receptor–Related Protein (LRP) Binds Secreted β–Amyloid Precursor Protein and Mediates Its Degradation," *Molec. Biol. Cell* 6(Suppl.):327a (Abstract 1901) (Jul. 1995).
Lorent, K. et al., "Expression in Mouse Embryos and in Adult Mouse Brain of Three Members of the Amyloid Precursor Protein Family, of the Alpha–2–Macroglobulin Receptor/Low Density Lipoprotein Receptor–Related Protein and of Its Ligands Apolipoprotein E, Lipoprotein Lipase, Alpha–2–Macroglobulin and the 40,000 Molecular Weight Receptor–Associated Protein," *Neuroscience* 65(4):1009–1025 (Apr. 1995).

Raffai, R. et al., "Molecular characterization of two monoclonal antibodies specific for the LDL receptor–binding site of human apolipoprotein E," *J. Lipid Res.* 36(9):1905–1918 (Sep. 1995).
Amann, E. and J. Brosius, "'ATG vectors' for regulated high–level expression of cloned genes in *Escherichia coli*," *Gene* 40:183–190 (1985).
Ammerer, G., "Expression of Genes in Yeast Using the ADCI Promoter," *Meth. Enzymol.* 101:192–201 (1983).
Ashcom, J. D. et al., "The Human $\alpha_2$–Macroglobulin Receptor: Identification of A 420–kD Cell Surface Glycoprotein Specific for The Activated Conformation of $\alpha_2$–Macroglobulin," *J. Cell. Biol.* 110(4):1041–1048 (Apr. 1990).
Battey, F. D. et al., "The 39–kDa Receptor–associated Protein Regulates Ligand Binding by the Very Low Density Lipoprotein Receptor," *J. Biol. Chem.* 269(37):23268–23273 (Sep. 1994).
Bayer, E. A. et al., "The Avidin–Biotin Complex in Affinity Cytochemistry," *Meth. Enzymol* 62:308–315 (1979).
Beidler, C. B. et al., "Cloning and High Level Expression of a Chimeric Antibody With Specificity For Human Carcinoembryonic Antigen," *J. Immunol.* 141(11):4053–4060 (Dec. 1988).
Beisiegel, U. et al., "The LDL–receptor–related protein, LRP, is an apolipoprotein E–binding protein," *Nature* 341:162–164 (Sep. 1989).
Better, M. et al., "*Escherichia coli* Secretion of an Active Chimeric Antibody Fragment," *Science* 240:1041–1043 (May 1988).
Brown, M. S. et al., "The low–density lipoprotein receptor–related protein: double agent or decoy?" *Curr. Op. Lipidol.* 2(2):65–72 (Apr. 1991).
Bu, G. et al., "Low density lipoprotein receptor–related protein/$\alpha_2$–macroglobulin receptor is an heptic receptor for tissue–type plasminogen activator," *Proc., Natl. Acad. Sci. USA* 89(16):7427–7431 (Aug. 1992).
Broach, J.R. et al., "Transformation in Yeast: Development of a Hybrid Cloning Vector and Isolation of the CAN1 Gene," *Gene* 8(1): 121–133 (Dec. 1979).
Carrasquillo, J. A. et al., "Indium–111 T101 Monoclonal Antibody is Superior to Iodine–131 T101 in Imaging of Cutaneous T–Cell Lymphoma," *J. Nucl. Med.* 28(3):281–287 (Mar. 1987).
Carter, P. et al., "High Level *Escherichia coli* Expresion and Production of a Bivalent Humanized Antibody Fragment," *Bio/Technology* 10:163–167 (Feb. 1992).

(List continued on next page.)

*Primary Examiner*—Patricia A. Duffy
*Attorney, Agent, or Firm*—Sterne, Kessler, Goldstein & Fox P.L.L.C.

[57] ABSTRACT

The present invention broadly relates to the treatment, diagnosis, and prophylactic prevention of Alzheimer's disease. More specifically, the present invention relates to methods and compositions for preventing the endocytosis and cellular internalization of integral membrane amyloid β-precursor protein (APP) and its subsequent catabolism by blocking or interfering with the association or binding of APP with members of the low density lipoprotein receptor family.

6 Claims, 11 Drawing Sheets

OTHER PUBLICATIONS

Chappell, D.A. et al., "Lipoprotein Lipase Induces Catabolism of Normal Triglyceride–rich Lipoproteins via the Low Density Lipoprotein Receptor–related Protein/$\alpha_2$–Macroglobulin Receptor in Vitro: A Process Facilitated by Cell–Surface Proteoglycans," *J. Biol. Chem.* 268(19):14168–14175 (Jul. 1993).

Davis, C. G. et al., "Acid–dependent ligand dissociation and recycling of LDL receptor mediated by growth factor homology region," *Nature* 326:760–765 (Apr. 1987).

Edge, M. D. et al., "Total synthesis of a human leukocyte interferon gene," *Nature* 292:756–762 (Aug. 1981).

Engvall, E. and P. Perlmann, "Enzyme–Linked Immunosorbent Assay, Elisa III. Quantitation of Specific Antibodies by Enzyme–Labeled Anti–Immunoglobulin in Antigen–Coated Tubes," *J. Immunol.* 109(1):129–135 (Jul. 1972).

Esteban, J. M. et al., "New Method for the Chelation of Indium–111 to Monoclonal Antibodies: Biodistribution and Imaging of Athymic Mice Bearing Human Colon Carcinoma Xenografts," *J. Nucl. Med.* 28(5):861–870 (May 1987).

Glenner, G. G. and C. W. Wong, "Alzheimer's Disease: Initial Report of the Purification and Characterization of a Novel Cerebrovascular Amyloid Protein," *Biochem. Biophys. Res. Comm.* 120(3):885–890 (May 1984).

Goate, A. et al., Segregation of a missense mutation in the amyloid precursor protein gene with familial Alzheimer's disease, *Nature* 349:704–706 (Feb. 1991).

Goding, J. W., "Conjugation of Antibodies With Fluorochromes: Modifications to the Standard Methods," *J. Immunol. Meth.* 13:215–226 (1976).

Hayden, F. G. et al., "Modification of experimental rhinovirus colds by receptor blockade," *Antiviral Res.* 9:233–247 (1988).

Hitzeman, R. A. et al., "Isolation and Characterization of the Yeast 3–Phosphoglycerokinase Gene (PKG) by an Immunological Screening Technique," *J. Biol. Chem.* 255(24):12073–12080 (Dec. 1980).

Hyman, B. T. et al., "Quantitative analysis of senile plaques in Alzheimer disease: Observation of log–normal size distribution and molecular epidemiology of differences associated with apolipoprotein E genotype and trisomy 21 (Down syndrome)," *Proc. Natl. Acad. Sci. USA* 92(8):3586–3590 (Apr. 1995).

Jensen, P. H. et al., "Purification of the human placental $\alpha_2$–macroglobulin receptor," *Febs Letts.* 255(2):275–280 (Sep. 1989).

Johnson–Wood, K. L. et al., "Identification of Secreted β–Amyloid Precursor Protein Binding Sites on Intact Human Fibroblasts," *Biochem. Biophys. Res. Comm.* 200(3):1685–1692 (May 1994).

Jones, P. T. et al., "Replacing the complementarity–determining regions in a human antibody with those from a mouse," *Nature* 321:522–525 (May 1986).

Kang, J. et al., "The precursor of Alzheimer's disease amyloid A4 protein resembles a cell–surface receptor," *Nature* 325:733–736 (Feb. 1987).

Kasprzak, A. A. et al., "Location of a Contact Site between Actin and Myosin in the Three–Dimensional Structure of the Acto–S1 Complex," *Biochem.* 28(23):9230–9238 (Nov. 1989).

Kawasaki, G. and D. G. Fraenkel, "Cloning of yeast glycolysis genes by complementation," *Biochem. Biophys. Res. Comm.* 108(3):1107–1112 (Oct. 1982).

Kennedy, J. H. et al., "Protein–Protein Coupling Reactions and the Applications of Protein Conjugates," *Clin. Chim. Acta* 70(1):1–31 (Jul. 1976).

Kingsman, A. J. et al., "Replication in *Saccharomyces cerevisiae* of Plasmid pBR313 Carrying DNA from the Yeast trp1 Region," *Gene* 7(2):141–153 (Oct. 1979).

Kishimoto, T. K. et al., "Identification of a human peripheral lymph node homing receptor: A rapidly down–regulated adhesion molecule," *Proc. Natl. Acad. Sci. USA* 87(6):2244–2248 (Mar. 1990).

Kitaguchi, N. et al., "Novel precursor of Alzheimer's disease amyloid protein shows protease inhibitory activity," *Nature* 331:530–532 (Feb. 1988).

Knauer, D. J. et al., "Protease Nexins: Cell–Secreted Proteins That Mediate the Binding, Internalization, and Degradation of Regulatory Serine Proteases," *J. Cell. Physiol.* 117(3):385–396 (Dec. 1983).

Knauer, D. J. and D. D. Cunningham, "Epidermal growth factor carrier protein binds to cells via a complex with released carrier protein nexin," *Proc. Natl. Acad. Sci. USA* 79(7):2310–2314 (Apr. 1982).

Kounnas, M. Z. et al., "The Cellular Internalization and Degradation of Hepatic Lipase Is Mediated by Low Density Lipoprotein Receptor–related protein and Requires Cell Surface Proteoglycans," *J. Biol. Chem.* 270(16):9307–9312 (Apr. 1995).

Kounnas, M. Z. et al., "The 39–kDa Receptor–associated Protein Interacts with Two Members of the Low Density Lipoprotein Receptor Family, $\alpha_2$–Macroglobulin Receptor and Glycoprotein 330," *J. Biol. Chem.* 267(29):21162–21166 (Oct. 1992).

Kounnas, M. Z. et al., "Low Density Lipoprotein Receptor–related Protein/$\alpha_2$–Macroglobulin Receptor Mediates Cellular Uptake of Pro–urokinase," *J. Biol. Chem.* 268(29):21862–21867 (Oct. 1993).

Kowal, R. C. et al., "Opposing Effects of Apolipoproteins E and C on Lipoprotein Binding to Low Density Lipoprotein Receptor–related protein," *J. Biol. Chem.* 265(18):10771–10779 (Jun. 1990).

Krieger, M. and J. Herz, "Structures and Functions of Multiligand Lipoprotein Receptors: Macrophage Scavenger Receptors and LDL Receptor–Related Protein (LRP)," *Annu. Rev. Biochem.* 63:601–637 (1994).

Lutz, Y. et al., "The Distribution of Two hnRNP–Associated Proteins Defined by a Monoclonal Antibody Is Altered In Heat–Shocked HeLa Cells," *Exp. Cell Res.* 175(1):109–124 (Mar. 1988).

Masters, C. L. et al., "Neuronal origin of a cerebral amyloid: neurofibrillary tangles of Alzheimer's disease contain the same protein as the amyloid of plaque cores and blood vessels," *EMBO J.* 4(11):2757–2763 (Nov. 1985).

Mikhailenko, I. et al., "Low Density Lipoprotein Receptor–related Protein/$\alpha_2$–Macroglobulin Receptor Mediates the Cellular Internalization and Degradation of Thrombospondin: A Process Facilitated by Cell–Surface Proteoglycans," *J. Biol. Chem.* 270(16):9543–9549 (Apr. 1995).

Mischak, H. et al., Characteristics of the Minor Group Receptor of Human Rhinoviruses, *Virol.* 163(1):19–25 (Mar. 1988).

Mischak, H. et al., "Detection of the Human Rhinovirus Minor Group Receptor on Renaturing Western Blots," *J. Gen. Virol.* 69(10):2653–2656 (Oct. 1988).

Moestrup, S. K. and J. Gliemann, "Purification of the Rat Hepatic $\alpha_2$–Macroglobulin Receptor as an Approximately 440–kDa Single Chain Protein," *J. Biol. Chem.* 264(26):15574–15577 (Sep. 1989).

Mullinax, R. L. et al., "Expression of a Heterodimeric Fab Antibody Protein in One Cloning Step," *BioTechniques* 12(6):864–869 (Jun. 1992).

Nykjçr, A. et al., "Purified $\alpha_2$–Macroglobulin Receptor/LDL Receptor–related Protein Binds Urokinase● Plasminogen Activator Inhibitor Type–1 Complex: Evidence that the $\alpha_2$–Macroglobulin Receptor Mediates Cellular Degradation of Urokinase Receptor–Bound Complexes," *J. Biol. Chem.* 267(21):14543–14546 (Jul. 1992).

Oltersdorf, T. et al., "The secreted form of the Alzheimer's amyloid precursor protein with the Kunitz domain is protease nexin–II," *Nature* 341:144–147 (Sep. 1989).

Orth, K. et al., "Complexes of tissue–type plasminogen activator and its serpin inhibitor plasminogen–activator inhibitor type 1 are internalized by means of the low density lipoprotein receptor–related protein/$\alpha_2$–macroglobulin receptor," *Proc. Natl. Acad. Sci. USA* 89(16):7422–7426 (Aug. 1992).

Perkins, A. C. et al., "The preparation and characterization of $^{111}$In–labelled 791T/36 monoclonal antibody for tumour immunoscintigraphy," *Eur. J. Nucl. Med.* 10:296–301 (1985).

Poirier, J. et al., "Apolipoprotein E polymorphism and Alzheimer's disease," *Lancet* 342:697–699 (Sep. 1993).

Poller, W. et al., "Differential Recognition of $\alpha_1$–Antitrypsin–Elastase and $\alpha_1$–Antichymotrypsin–Cathepsin G Complexes by the Low Density Lipoprotein Receptor–related Protein," *J. Biol. Chem.* 270(6):2841–2845 (Feb. 1995).

Rebeck, G. W. et al., "Multiple, Diverse Senile Plaque–associated Proteins Are Ligands of an Apolipoprotein E Receptor, the $\alpha_2$–Macroglobulin Receptor/Low–Density–Lipoprotein Receptor–related Protein," *Ann. Neurol.* 37(2):211–217 (Feb. 1995).

Rebeck, G. W. et al., "Apolipoprotein E in Sporadic Alzheimer's Disease: Allelic Variation and Receptor Interactions," *Neuron* 11(4):575–580 (Oct. 1993).

Rëther, U. and B. Müller–Hill, "Easy identification of cDNA clones," *EMBO J.* 2(10):1791–1794 (1983).

Saito, A. et al., "Complete cloning and sequencing of rat gp330/"megalin," a distinctive member of the low density lipoprotein receptor gene family," *Proc. Natl. Acad. Sci. USA* 91(21):9725–9729 (Oct. 1994).

Saunders, A. M. et al., "Association of apolipoprotein E allele ε4 with late–onset familial and sporadic Alzheimer's disease," *Neurology* 43(8):1467–1472 (Aug. 1993).

Schmaier, A. H. et al., "Protease Nexin–2/Amyloid β Protein Precursor: A Tight–binding Inhibitor of Coagulation Factor IXa," *J. Clin. Invest* 92(5):2540–2545 (Nov. 1993).

Schuurs, A. H. W. M. and B. K. Van Weemen, "Enzyme–Immunoassay," *Clin. Chim. Acta* 81:1–40 (1977).

Shimatake, H. and M. Rosenberg, "Purified λ regulatory protein CII positively activates promoters for lysogenic development," *Nature* 292:128–132 (Jul. 1981).

Slunt, H. H. et al., "Expression of a Ubiquitous, Cross–reactive Homologue of the Mouse β–Amyloid Precursor Protein (APP)," *J. Biol. Chem.* 269(4):2637–2644 (Jan. 1994).

Stanley, K. K. and J. P. Luzio, "Construction of a new family of high efficiency bacterial expression vectors: identification of cDNA clones coding for human liver proteins," *EMBO J.* 3(6):1429–1434 (Jun. 1984).

Sternberger, L. A. et al., "The Unlabeled Antibody Enzyme Method of Immunohistochemistry: Preparation and Properties of Soluble Antigen–Antibody Complex (Horseradish Peroxidase–Antihorseradish Peroxidase) and Its Use In Identification of Spirochetes," *J. Histochem. Cytochem.* 18(5):315–333 (May 1970).

Stinchcomb, D. T. et al., "Isolation and characterisation of a yeast chromosomal replicator," *Nature* 282:39–43 (Nov. 1979).

Strickland, D. K. et al., "Primary Structure of $\alpha_2$–Macroglobulin Receptor–associated Protein: Human Homologue of a Heymann Nephritis Antigen," *J. Biol. Chem.* 266(20):13364–13369 (Jul. 1991).

Strittmatter, W. J. et al., "Apolipoprotein E: High–avidity binding to β–amyloid and increased frequency of type 4 allele in late–onset familial Alzheimer disease," *Proc. Natl. Acad. Sci. USA* 90(5):1977–1981 (Mar. 1993).

Studier, F. W. and B. A. Moffatt, "Use of Bacteriophage T7 RNA Polymerase to Direct Selective High–level Expression of Cloned Genes," *J. Mol. Biol.* 189(1):113–130 (May 1986).

Takahashi, S. et al., "Rabbit very low density lipoprotein receptor: A low density lipoprotein receptor–like protein with distinct ligand specificity," *Proc. Natl. Acad. Sci. USA* 89(19):9252–9256 (Oct. 1992).

Tanzi, R. E. et al., "Protease inhibitor domain encoded by an amyloid protein precursor mRNA associated with Alzheimer's disease," *Nature* 331:528–530 (Feb. 1988).

Tanzi, R. E. et al., "Amyloid β Protein Gene: cDNA, mRNA Distribution, and Genetic Linkage Near the Alzheimer Locus," *Science* 235:880–884 (Feb. 1987).

Tschumper, G. and J. Carbon, "Sequence of a yeast DNA fragment containing a chromosomal replicator and the TRP1 gene," *Gene* 10(2):157–166 (Jul. 1980).

Van Nostrand, W. E. et al., "Protease nexin–II, a potent anti–chymotrypsin, shows identity to amyloid β–protein precursor," *Nature* 341:546–549 (Oct. 1989).

Van Nostrand, W. E. et al., "Immunopurification and Protease Inhibitory Properties of Protease Nexin–2/Amyloid β–Protein Precursor," *J. Biol. Chem.* 265(17):9591–9594 (Jun. 1990).

Van Nostrand, W. E. and D. D. Cunningham, "Purification of Protease Nexin II from Human Fibroblasts," *J. Biol. Chem.* 262(18):8508–8514 (Jun. 1987).

Verhoeyen, M. et al., "Reshaping Human Antibodies: Grafting an Antilysozyme Activity," *Science* 239:1534–1536 (Mar. 1988).

Warshawsky, I. et al., "Binding Analysis of Amino–terminal and Carboxyl–terminal Regions of the 39–kDa Protein to the Low Density Lipoprotein Receptor–related Protein," *J. Biol. Chem.* 269(5):3325–3330 (Feb. 1994).

Warshawsky, I. et al., "The low density lipoprotein receptor–related protein mediates the cellular degradation of tissue factor pathway inhibitor," *Proc. Natl. Acad. Sci. USA* 91(14):6664–6668 (Jul. 1994).

Wasco, W. et al., "Isolation and characterization of APLP2 encoding a homologue of the Alzheimer's associated amyloid β protein precursor," *Nature Genetics* 5(1):95–100 (Sep. 1993).

Wasco, W. et al., "Identification of a mouse brain cDNA that encodes a protein related to the Alzheimer disease–associated amyloid β protein precursor," *Proc. Natl. Acad. Sci. USA* 89(22):10758–10762 (Nov. 1992).

Williams, S. E. et al., "A Novel Mechanism for Controlling the Activity of $\alpha_2$–Macroglobulin Receptor/Low Density Lipoprotein Receptor–related Protein: Multiple Regulatory Sites for 39–kDa Receptor–Associated Protein," *J. Biol. Chem.* 267(13):9035–9040 (May 1992).

Willnow, T. E. et al., "Low Density Lipoprotein Receptor––related Protein and gp330 Bind Similar Ligands, Including Plasminogen Activator–Inhibitor Complexes and Lactoferrin, an Inhibitor of Chylomicron Remnant Clearance," *J. Biol. Chem.* 267(36):26172–26180 (Dec. 1992).

Yamamoto, T. et al., "The Human LDL Receptor: A Cysteine–Rich Protein with Multiple Alu Sequences in Its mRNA," *Cell* 39(1):27–38 (Nov. 1984).

Yokode, M. et al., "Cytoplasmic Sequence Required for Basolateral Targeting of LDL Receptor in Livers of Transgenic Mice," *J. Cell Biol.* 117(1):39–46 (Apr. 1992).

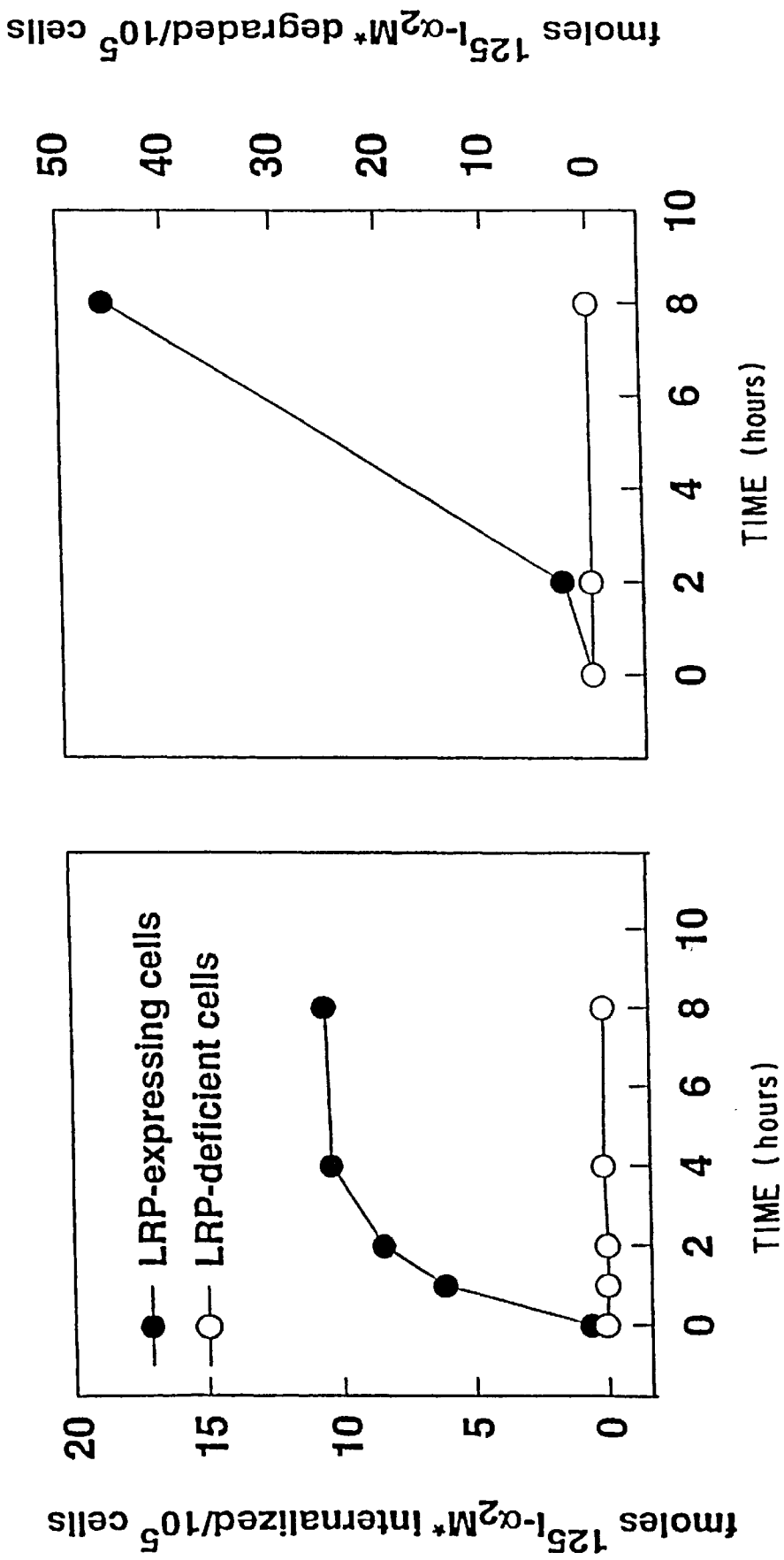

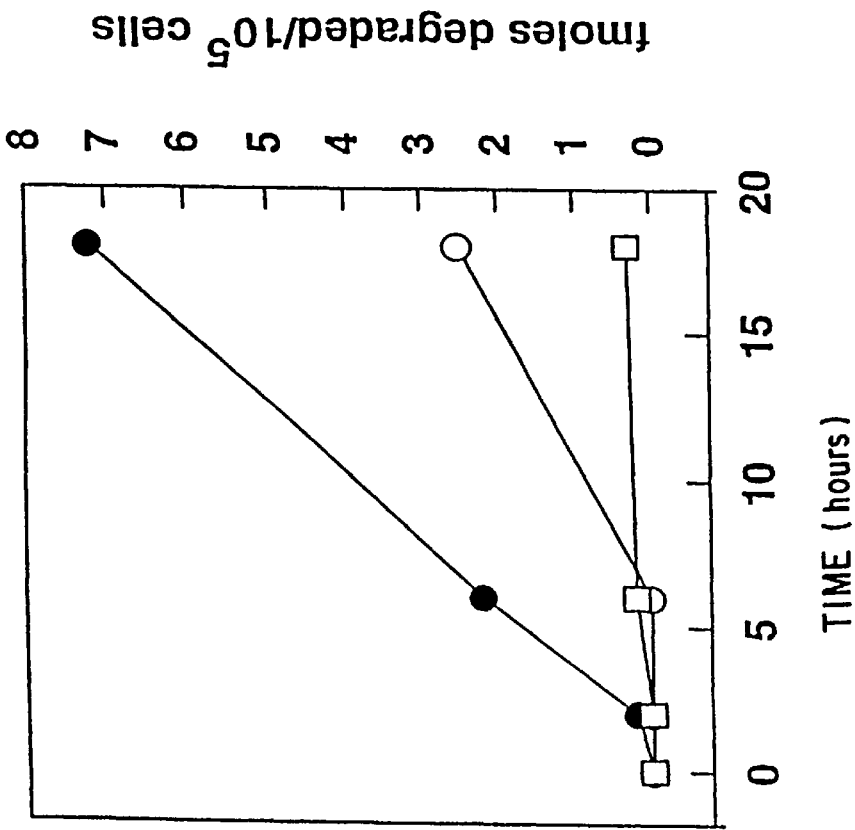
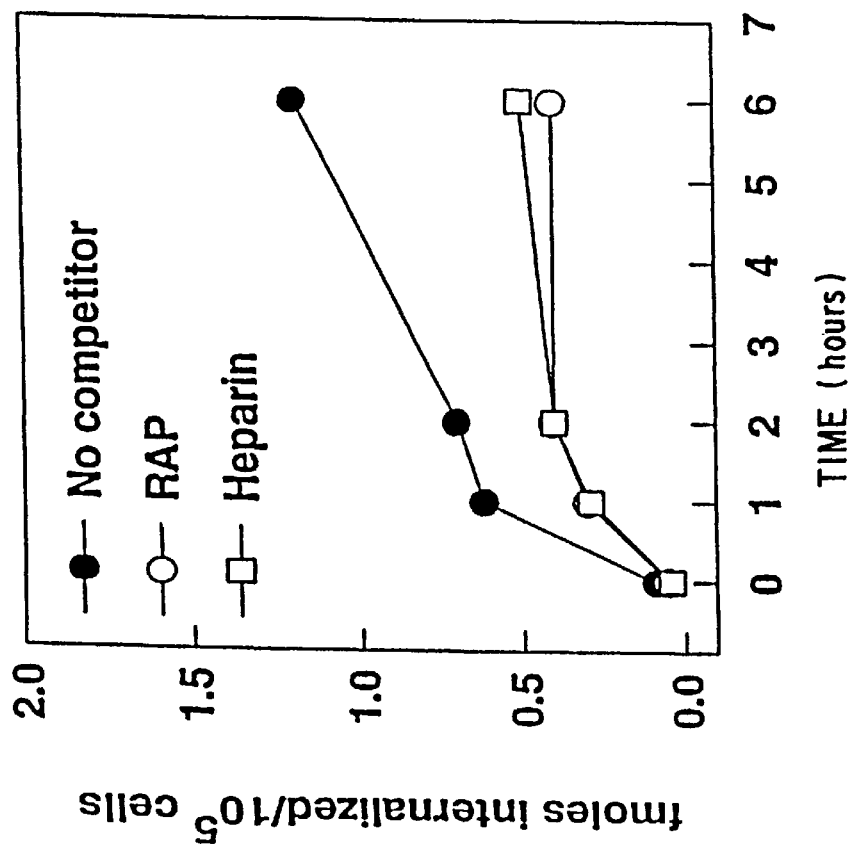
FIG. 3A
FIG. 3B

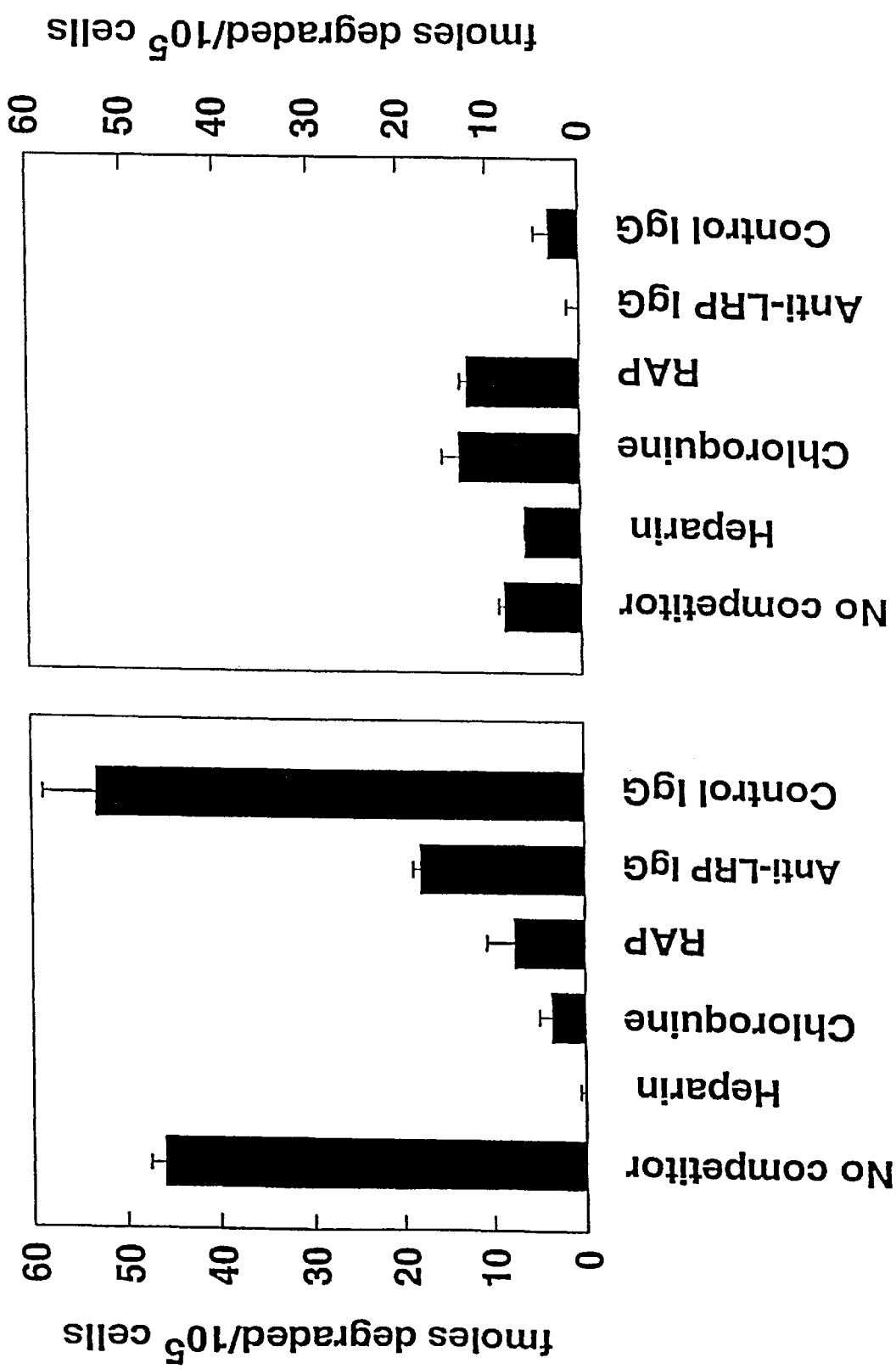

MODULATORS OF EXPRESSION AND FUNCTION OF LRP IN ALZHEIMER'S DISEASE

This application claims priority to provisional application Ser. No. 60/001,600, filed Jul. 25, 1995, now abandoned.

RIGHTS OF THE UNITED STATES GOVERNMENT

Part of the work performed during development of this invention utilized U.S. government funds in the form of grant GM42581, grant HL50787, and grant AG12406, all from the National Institutes of Health. The U.S. government therefore has certain rights in one or more embodiments of this invention.

FIELD OF THE INVENTION

The present invention broadly relates to the treatment, diagnosis, and prophylactic prevention of Alzheimer's disease. More specifically, the present invention relates to methods and compositions for preventing the endocytosis and cellular internalization of integral membrane amyloid β-precursor protein (APP) and its subsequent catabolism by blocking or interfering with the association or binding of APP with members of the low density lipoprotein receptor family.

BACKGROUND OF THE INVENTION

Alzheimer's disease (AD) is a late onset neurodegenerative disorder characterized by the extracellular deposition of insoluble aggregates composed of the 40 to 42 amino acid Aβ peptide in the brain (Glenner and Wong, *Biochem. Biophys. Res. Commun.* 120:885–890 (1984); Masters et al., *EMBO J.* 4:2757–2763 (1985)). Aβ peptide is derived from an integral membrane protein termed amyloid β-protein precursor protein (APP) (Tanzi et al., *Science* 235:880 (1987); Kang et al., *Nature* 325:733–736 (1987)). The function and metabolism of APP have been the subject of intensive study due to the fact that mutations in APP are associated with an autosomal dominant form of AD, (Goate et al., *Nature* 349:704–707 (1991)) and over-production of APP is the presumptive cause of AD in trisomy 21 (Tanzi et al., *Science* 235:880 (1987); Hyman et al., *Proc. Natl. Acad. Sci. USA* 92:3586–3590 (1995)). Multiple APP isoforms can be generated by alternatively splicing of mRNAs. The major isoforms in brain are APP695, APP751, and APP770 containing 695, 751 and 770 amino acids, respectively. These isoforms are transmembranous proteins having large extracellular regions, with hydrophobic membrane spanning domains and short cytoplasmic segments. APP is also a member of an evolutionary conserved family of proteins which include the APP-like proteins, APLP1 and APLP2 (Wasco et al., *Proc. Natl. Acad. Sci. USA* 89:10758–10762 (1992); Wasco et al., *Nature Genet.* 5:95–100 (1993); Slunt et al., *J. Biol. Chem.* 269:2637–2644 (1994)).

Secreted forms of APP are generated by proteolytic cleavages within their extracellular domain close to the transmembrane region. The extracellular regions of APP751, APP770, and APLP2 each contain a Kunitz protease inhibitor (KPI) domain encoded by an alternatively-transcribed exon (Kitaguchi et al., *Nature* 331:530–532 (1988); Tanzi et al., *Nature* 331:528–530 (1988); Wasco et al, *Nature Genet.* 5:95–100 (1993); Slunt et al., *J. Biol. Chem.* 269:2637–2644 (1994)). Secreted forms of APP having the KPI domain correspond to a protease inhibitor that has been identified separately and named protease nexin II (APP/PN-2) (Van Nostrand and Cunningham, *J. Biol. Chem.* 262:8508–8514 (1987); Oltersdorf et al., *Nature* 341:144–147 (1989); Van Nostrand et al., *Nature* 341:546–549 (1989)), a potent inhibitor of the blood coagulation factors IXa (Schmaier et al., *J. Clin. Invest.* 92:2540–2545 (1993)) and XIa (Van Nostrand et al., *J. Biol. Chem.* 265:9591–9594 (1990)). APP/PN-2 binds with high affinity to cultured fibroblasts (Johnson-Wood et al., *Biochem. Biophys. Res. Commun.* 200:1685–1692 (1994)), and APP/PN-2:proteinase complexes are internalized and degraded by cultured cells (Knauer and Cunningham, *Proc. Natl. Acad. Sci. USA* 79:2310–2314 (1982); Knauer et al., *J. Cell. Physiol.* 117:385–396 (1983)) although the mechanism for this process is unknown. Recent studies have identified the low density lipoprotein receptor-related protein (LRP) as the receptor responsible for the catabolism of another Kunitz-type inhibitor, tissue factor pathway inhibitor (TFPI) (Warshawsky et al., *Proc. Natl. Acad. Sci. USA* 91:6664–6668 (1994)).

LRP is a large multiligand receptor (Krieger and Herz, *Annu. Rev. Biochem.* 63:601–637 (1994)) that is a member of the LDL receptor family, which also includes the LDL receptor (Yamamoto et al., *Cell* 39:27–38 (1984)), the VLDL receptor (Takahashi et al., *Proc. Natl. Acad Sci. USA* 89:9252–9256 (1992)), and glycoprotein 330 (Saito et al., *Proc. Natl. Acad. Sci. USA* 91:9725–9729 (1994)). A 39 kDa protein, termed the receptor associated protein (RAP) (Strickland et al., *J. Biol. Chem.* 266:13364–13369 (1991)) binds to members of the LDL receptor family (Williams et al., *J. Biol. Chem.* 267:9035–9040 (1992); Kounnas et al., *J. Biol. Chem.* 267:21162–21166 (1992); Battey et al., *J. Biol. Chem.* 269:23268–23273 (1994)) and blocks their ligand binding capacity. LRP mediates the cellular uptake and subsequent degradation of proteinases, such as tissue-type plasminogen activator (Bu et al., *Proc. Natl. Acad Sci. USA* 89:7427–7431 (1992)) and urokinase-type plasminogen activator (Kounnas et al., *J. Biol. Chem.* 268:21862–21867 (1993)), proteinase-inhibitor complexes, such as $\alpha_2$-macroglobulin-proteinase complexes (Ashcom et al., *J. Cell Biol.* 110:1041–1048 (1990); Moestrup and Gliemann, *J. Biol. Chem.* 264:15574–15577 (1989)), serpin-proteinase complexes (Orth et al., *Proc. Natl. Acad. Sci. USA* 89:7422–7426 (1992); Nykjær et al., *J. Bio. Chem.* 267:14543–14546 (1992); Poller et al, *J. Biol. Chem.* 270:2841–2845 (1995)), matrix proteins, such as thrombospondin (Mikhailenko et al., *J. Biol. Chem.* 270:9543–9549 (1995)), apolipoprotein E (apoE)-enriched lipoproteins (Kowal et al, *J. Biol. Chem.* 265:10771–10779 (1990); Beisiegel et al., *Nature* 341:162–164 (1989)), hepatic lipase (Kounnas et al., *J. Biol. Chem.* 270:9307–9312 (1995)) and lipoprotein lipase (Chappell et al., *J. Biol. Chem.* 268:14168–14175 (1993)).

LRP is expressed in many tissues and is a major apoE receptor in the central nervous system (Rebeck et al., *Neuron* 11:575–580 (1993)). Genetic data implicate inheritance of the ∈4 allele of apoE as a risk factor in AD (Strittmatter et al., *Proc. Natl. Acad. Sci USA* 90:1977–1981 (1993); Rebeck et al., *Neuron* 11:575–580 (1993); Poirier et al., *Lancet* 342:697–699 (1993); Saunders et al., *Neurology* 43:1467–1472 (1993)). A possible involvement of LRP in AD is suggested in part by the observation that LRP, as well as apoE and other LRP ligands, decorate senile plaques (Rebeck et al., *Ann. Neurol.* 37:211–217 (1995)).

The ability of LRP to mediate the cellular catabolism of TFPI, a KPI-containing protein, led to the investigation of the role of LRP in the catabolism of $APP_s770$. The present inventors have found that LRP is capable of binding and mediating the internalization and degradation of $APP_s770$ as well as its complexes with proteinases.

Because catabolism of APP has been shown to generate the Aβ peptide, which is believed to be the causative agent of Alzheimer's Disease, there is a need for compositions and methods which reduce the interaction, cellular internalization and subsequent catabolism of APP.

SUMMARY OF THE INVENTION

Accordingly, it is an object of the present invention to provide agents which bind to APP or LDL-receptor family members and reduce the interaction, cellular internalization, and subsequent catabolism of APP. Other objects, features and advantages of the present invention will be set forth in the detailed description of preferred embodiments that follows, and in part will be apparent from the description or may be learned by practice of the invention. These objects and advantages of the invention will be realized and attained by the compositions methods particularly pointed out in the written description and claims hereof.

A first embodiment of the present invention therefore relates to agents which bind to the APP-binding site on the LRP particle (Group I agents) and agents which bind to the LRP-binding site found on APP (Group II agents).

An additional embodiment of the present invention relates to DNA molecules which encode peptides and antibodies that are Group I agents and/or Group II agents and to host organisms that have been transformed with the DNA molecules of the present invention.

The present invention also relates to processes for preparing DNA molecules which encode a functional derivative or a fragment of LRP, RAP or APP. These processes can yield DNA sequences which are inserted into a vector DNA containing expression control sequences in such a way that the expression control sequences regulate the expression of the inserted DNA.

A further embodiment of the present invention relates to methods for preparing polypeptides that are functional derivatives of LRP which comprise taking the polypeptide from the native receptor molecule by enzymatic, such as proteolytic, or chemical, such as reductive, treatment.

An additional embodiment of the invention relates to a process for preparing Group I agents which are a functional derivative of APP or RAP which comprise expressing a recombinant DNA molecule according to the invention.

The present invention further relates to Group II agents which are antibodies, or an antibody fragment containing the antigen binding domain, that bind to the LRP binding site found on APP.

Another embodiment of the present invention relates to processes for preparing Group II agents which are a functional derivative of LRP which comprise expressing a recombinant DNA molecule according to the invention.

The present invention additionally relates to hybrid cell lines that secrete monoclonal antibodies against the LDL-receptor protein which interfere with APP attachment to the LRP receptor.

An additional embodiment of the present invention includes the use of Group I agents and/or Group II agents for qualitatively and/or quantitatively determining or purifying the presence of LRP which is found in a sample.

A further embodiment of the present invention includes a test kit for determining whether a polypeptide is a Group I agent and/or a Group II agent, this kit comprising a carrier means having in close confinement therein one or more container means at least one of which contains an antibody that binds to the LRP binding site found on APP.

Another embodiment of the present invention relates to processes for preparing antibodies that bind to the LRP binding site found on APP, in which a host animal is immunized with one or more polypeptides of Group I and/or Group II, the B-lymphocytes of these host animals are fused with myeloma cells, and a hybrid cell line secreting the monoclonal antibody is subcloned and cultivated.

An additional embodiment of the present invention relates to the use of Group I agents and/or Group II agents, or the native receptor molecules of the LDL-receptor family or pharmaceutically suitable salts thereof, for the therapeutic or prophylactic treatment of the human body.

The invention also relates to methods for reducing the rate of onset or the severity of Alzheimer's disease, comprising administering to an animal, such as a human, one or more Group I agents and/or one or more Group II agents in an amount effective to reduce the rate of APP attachment to its receptor.

A further embodiment of the present invention relates to pharmaceutical compositions for therapeutic treatment of Alzheimer's disease, comprising one or more of Group I agents and/or one or more Group II agents and/or the native receptor molecule of the LDL-receptor family and a pharmaceutically acceptable carrier.

An additional embodiment of the invention relates to the use of LRP for inhibiting the binding of natural ligands to a member of the LDL-receptor family of proteins.

An alternative embodiment of the present invention relates to methods for identifying substances which inhibit the binding of a ligand (RAP) or APP to a protein derived from the LDL-receptor family, comprising the steps of:

a) incubating the receptor, or a soluble form of the receptor, with RAP or APP in the presence of a potential inhibitor substance; and b) determining the extent of binding of RAP or APP to the receptor or receptor fragment.

Another embodiment of the present invention relates to methods for detecting receptors of the LDL-receptor family, comprising the steps of:

a) incubating a substance derived from a fragment of RAP or APP which contains a binding activity for the receptor with a sample; and b) determining the extent of binding of the RAP or APP material to the sample.

A further embodiment of the present invention relates to methods for supplying a therapeutically active substance into a carrying cell, characterized in that a) a fragment of RAP or APP with a binding activity on the LDL-receptor is coupled with the therapeutic substance; and b) the said material is added to the corresponding cell material, bound to the receptor and in this way the therapeutically active substance is introduced into the cell.

It is to be understood that both the foregoing general description and the following detained description are exemplary and explanatory only and are intended to provide further explanation of the invention as claimed.

BRIEF DESCRIPTION OF THE FIGURES

FIGS. 2A–D show the internalization and degradation of LDL by both LRP-containing and LRP-deficient fibroblasts (panels A and B) and the internalization and degradation of $\alpha_2$-macroglobulin by LRP-containing fibroblasts and the lack of both internalization and degradation of $\alpha_2$-macroglobulin by LDL-deficient fibroblasts (panels C and D).

FIGS. 3A–D show the internalization and degradation of APP by LRP-containing fibroblasts (panels A and B) and the substantially lower level of internalization and degradation of APP by LRP-deficient fibroblasts (panels C and D). Note the inhibition of internalization of APP by the addition of heparin (panels A, B, C and D).

FIGS. 4A–B show the inhibition of APP degradation by LRP-binding ligands in LRP-containing fibroblasts (panel A) and the lesser effect of these ligands on APP degradation by LRP-deficient fibroblasts (panel B).

DETAILED DESCRIPTION OF THE PREFERRED EMBODIMENTS

Figure 1A:
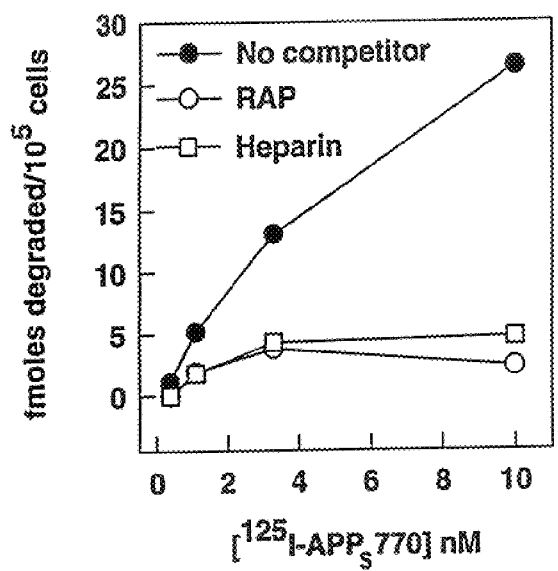
FIGS. 1A–D show the catabolism of APP by fibroblasts containing LRP (panel A) compared to the absence of catabolism of APP by fibroblasts deficient in LRP (panel B) and the absence of catabolism of APP lacking the KPI domain by either LRP-containing or LRP-deficient fibroblasts (panels C and D). Note the inhibition of catabolism of APP by the addition of RAP in fibroblasts containing LRP (panel A).
Figure 1B:
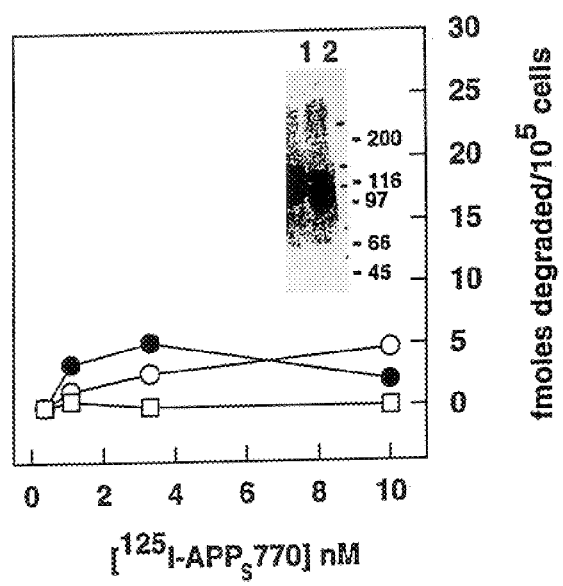
Figure 1C:
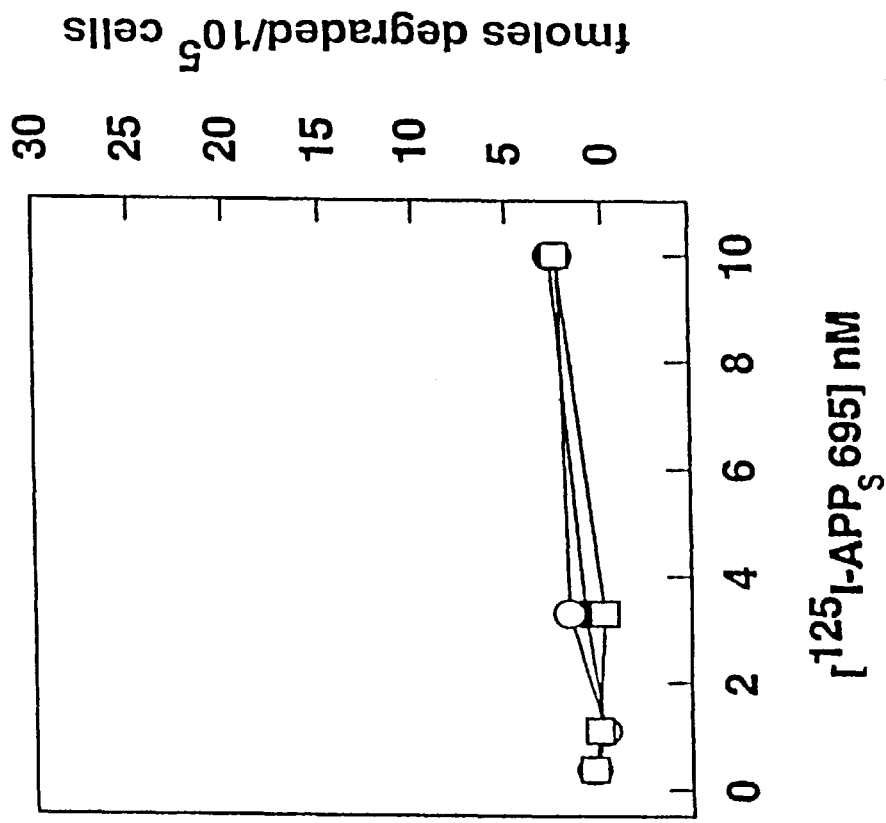
Figure 1D:
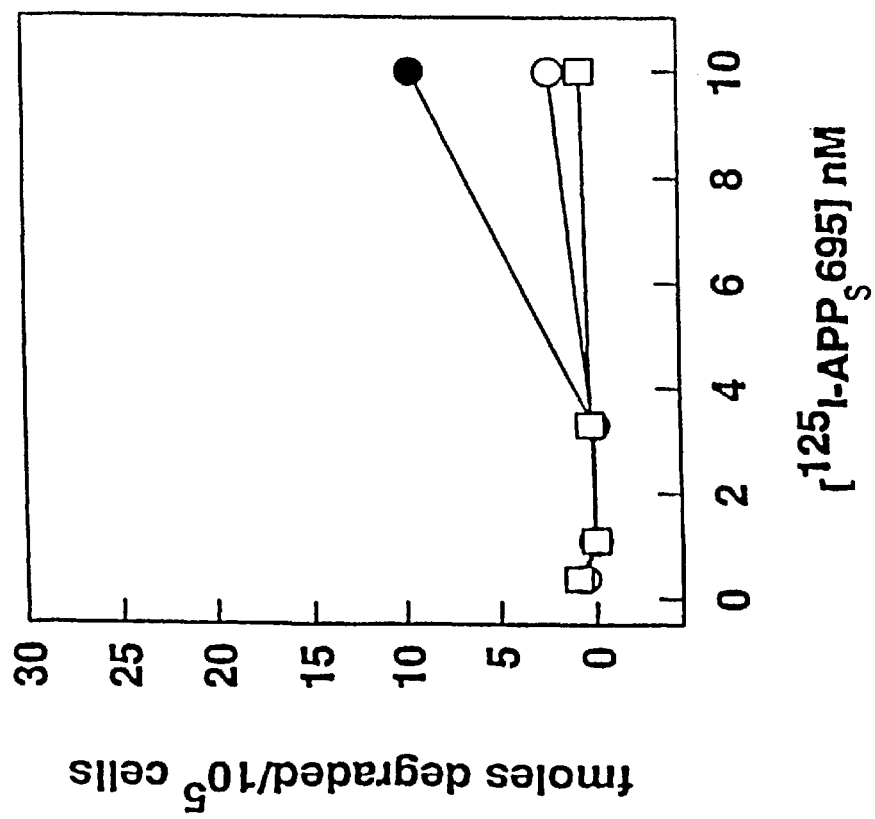
Figure 2B:
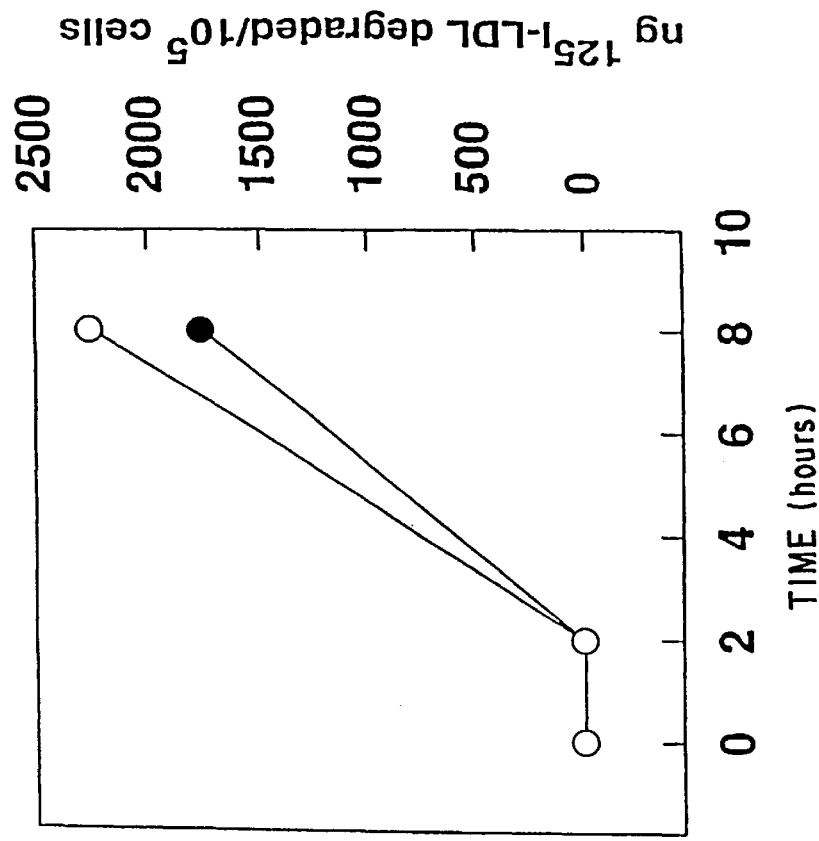
Figure 2A:
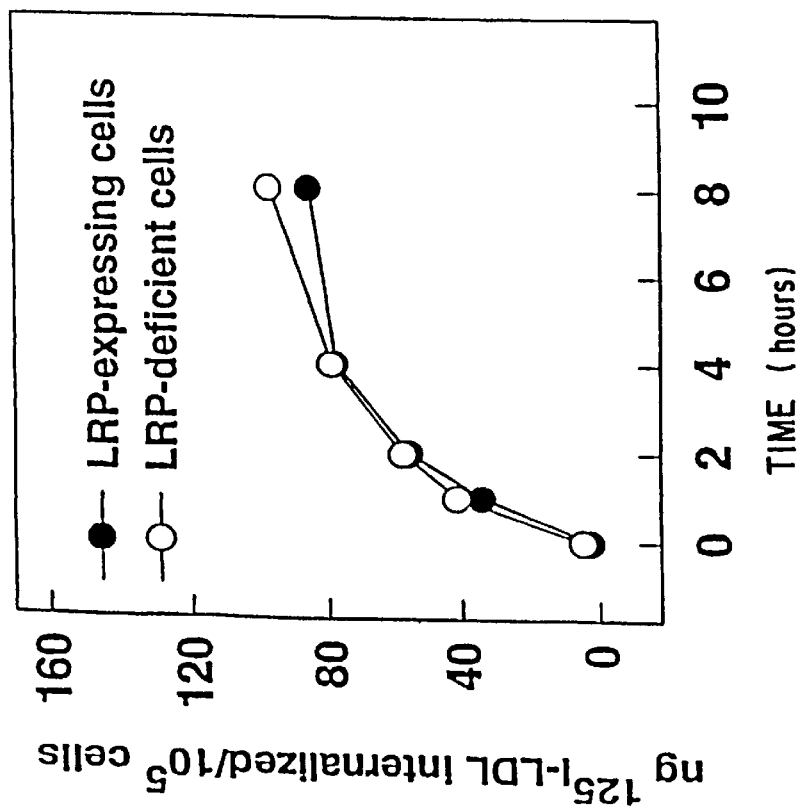
Figures 3C, 3D:
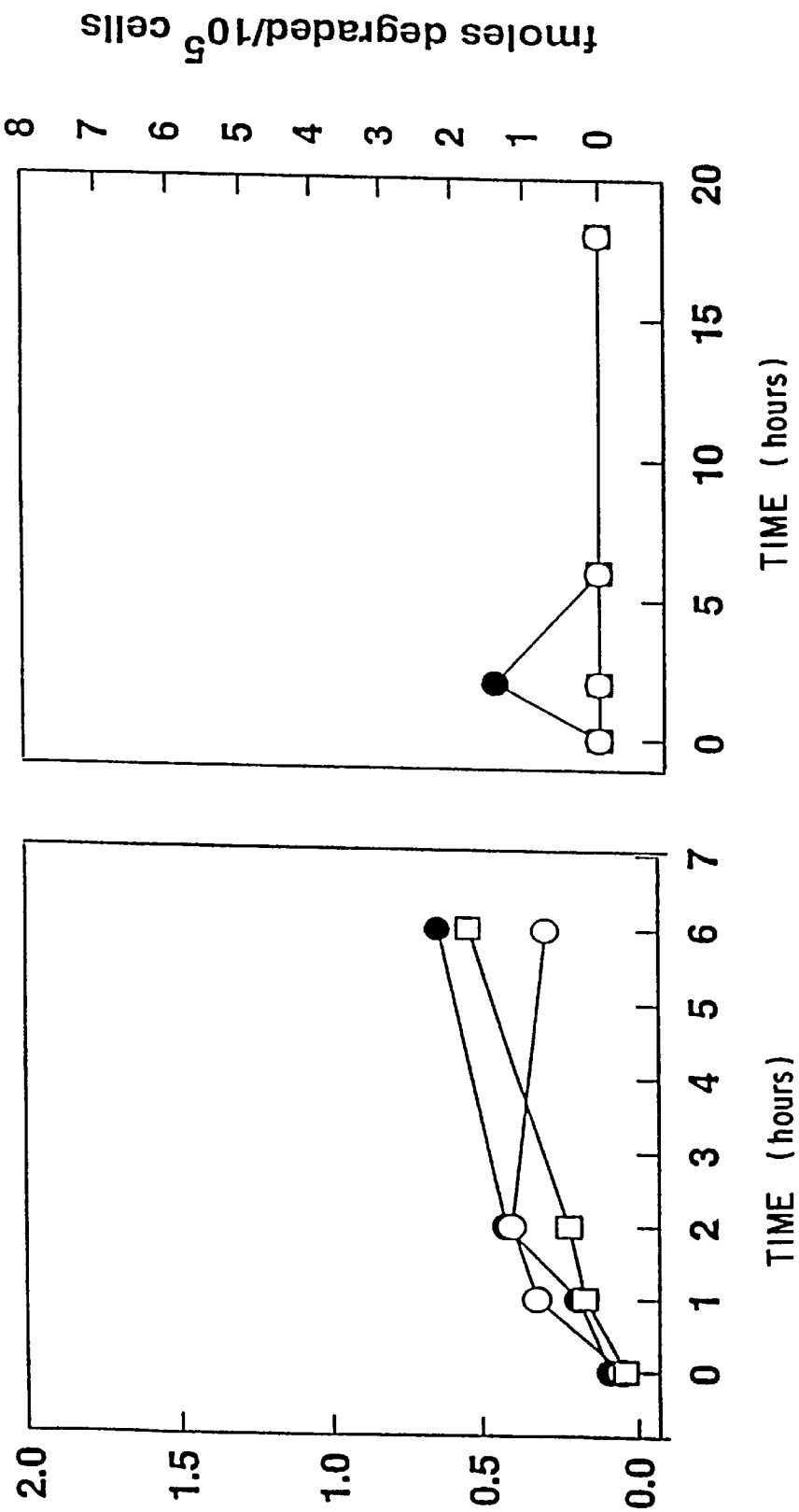
Figure 5B:
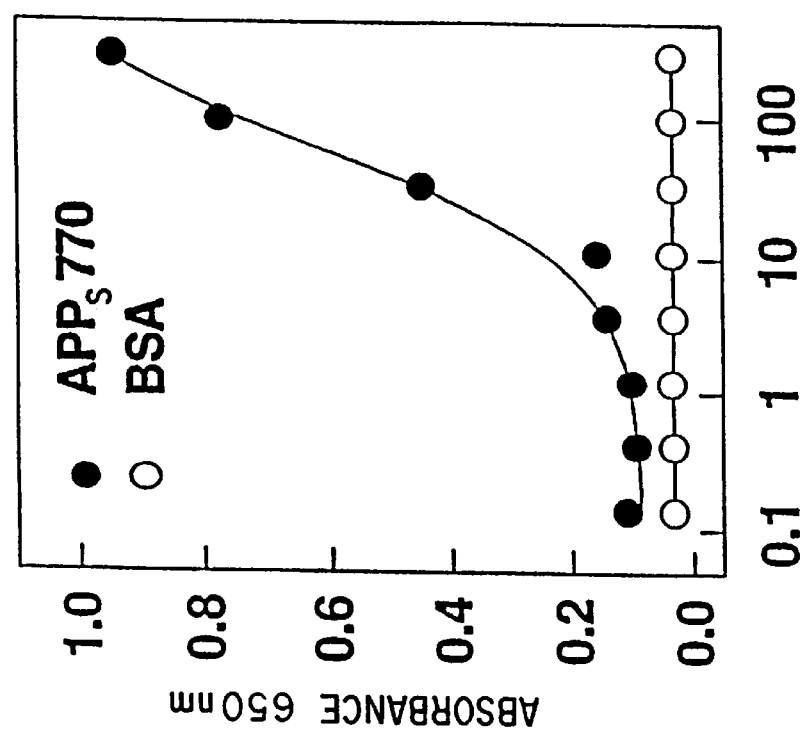
FIGS. 5A–C show the direct ability of APP to bind LRP as measured by enzyme-linked immunosorbant assay (ELISA) using anti-APP (panel A) as compared to the amount of LRP available for binding (panel B). Note the inhibition of APP binding by RAP, an LRP ligand (panel C).
Figure 5A:
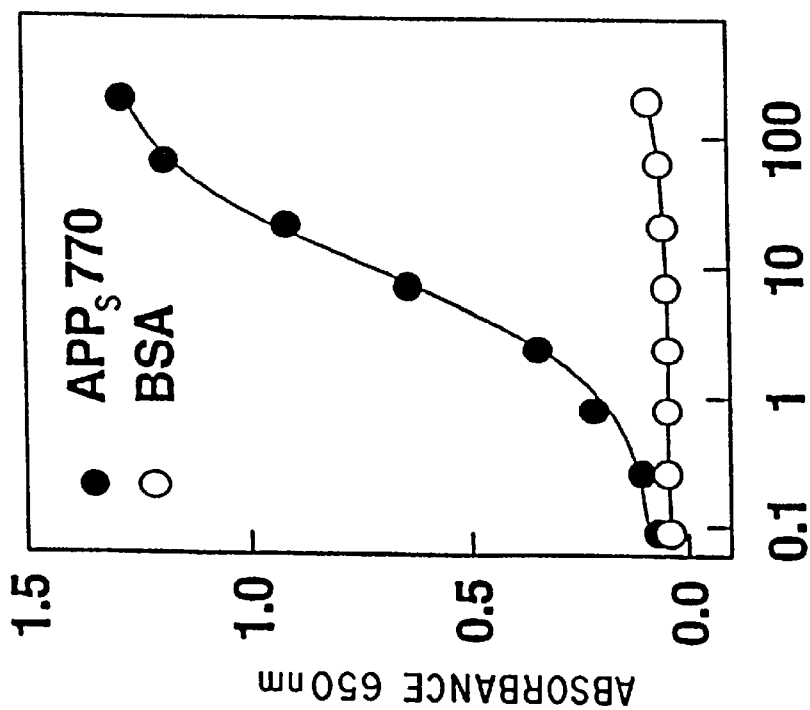
Figure 5C:
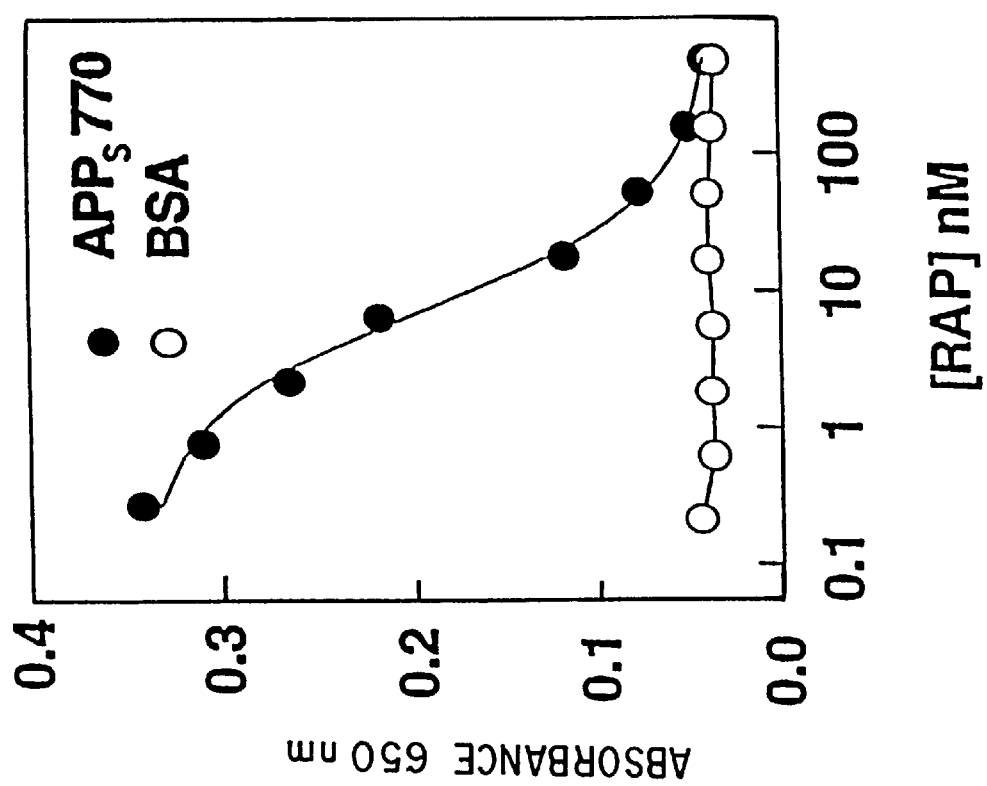
Figure 6B:
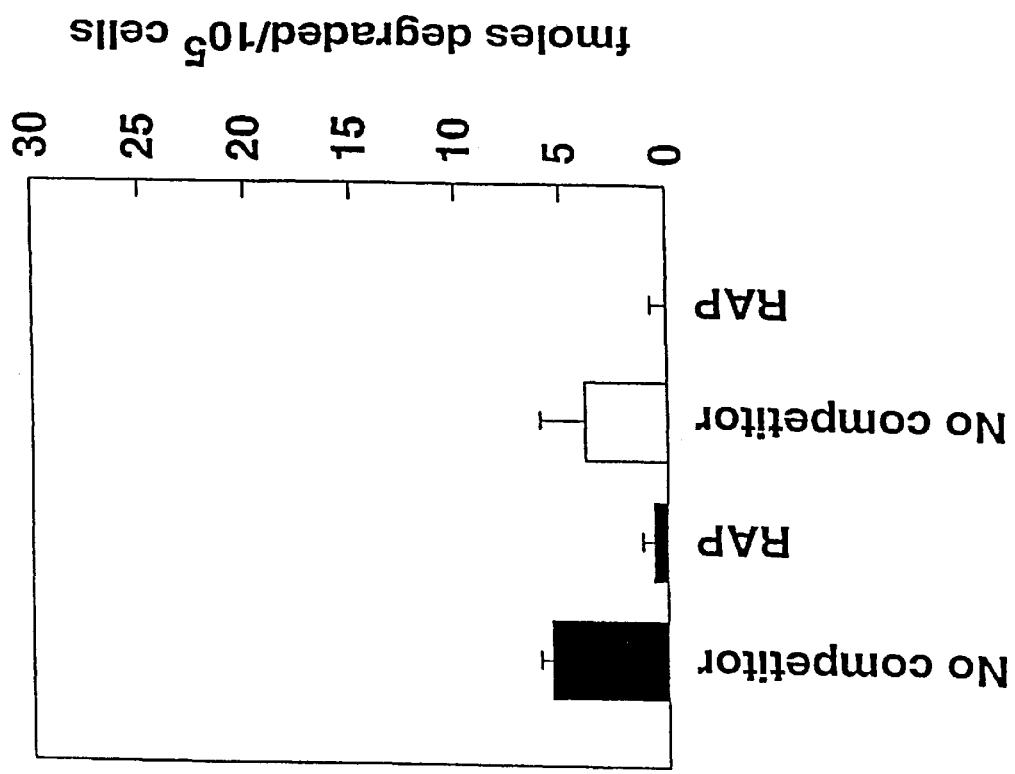
FIGS. 6A–B show the enhancement of degradation of APP in LRP-containing fibroblasts by coupling with coagulation factor IXa (panel A) as compared to the degradation of APP in LRP-deficient fibroblasts (panel B). Note the inability of this complexing to avoid inhibition of degradation by RAP (panel A).
Figure 6A:
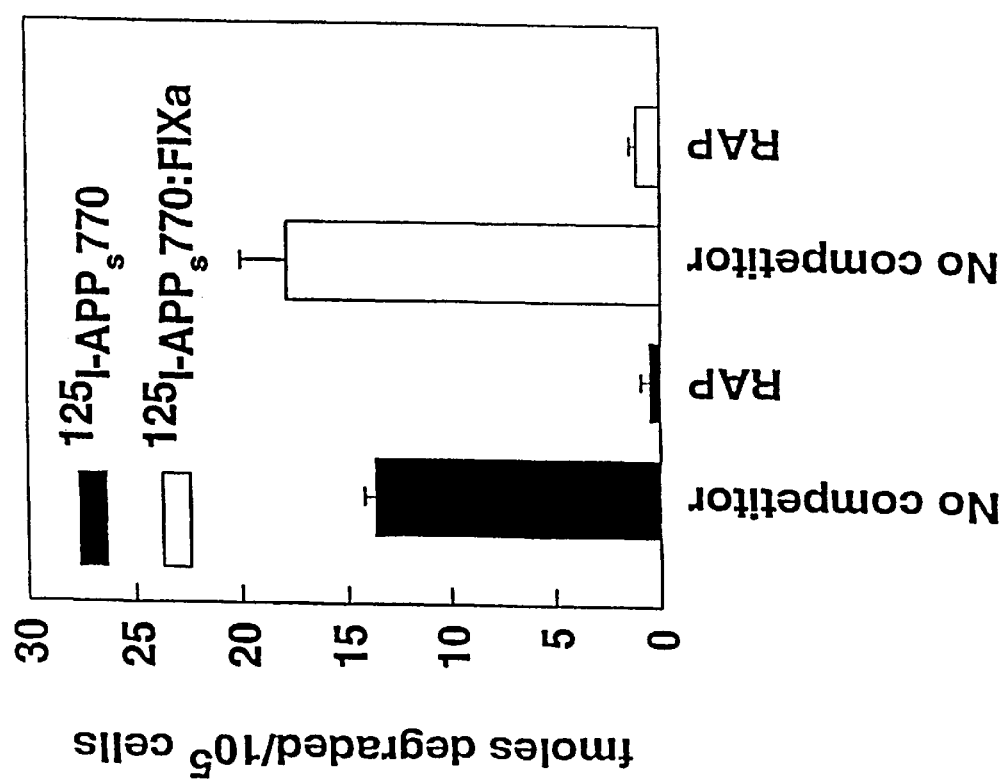
Figures 7A, 7B:
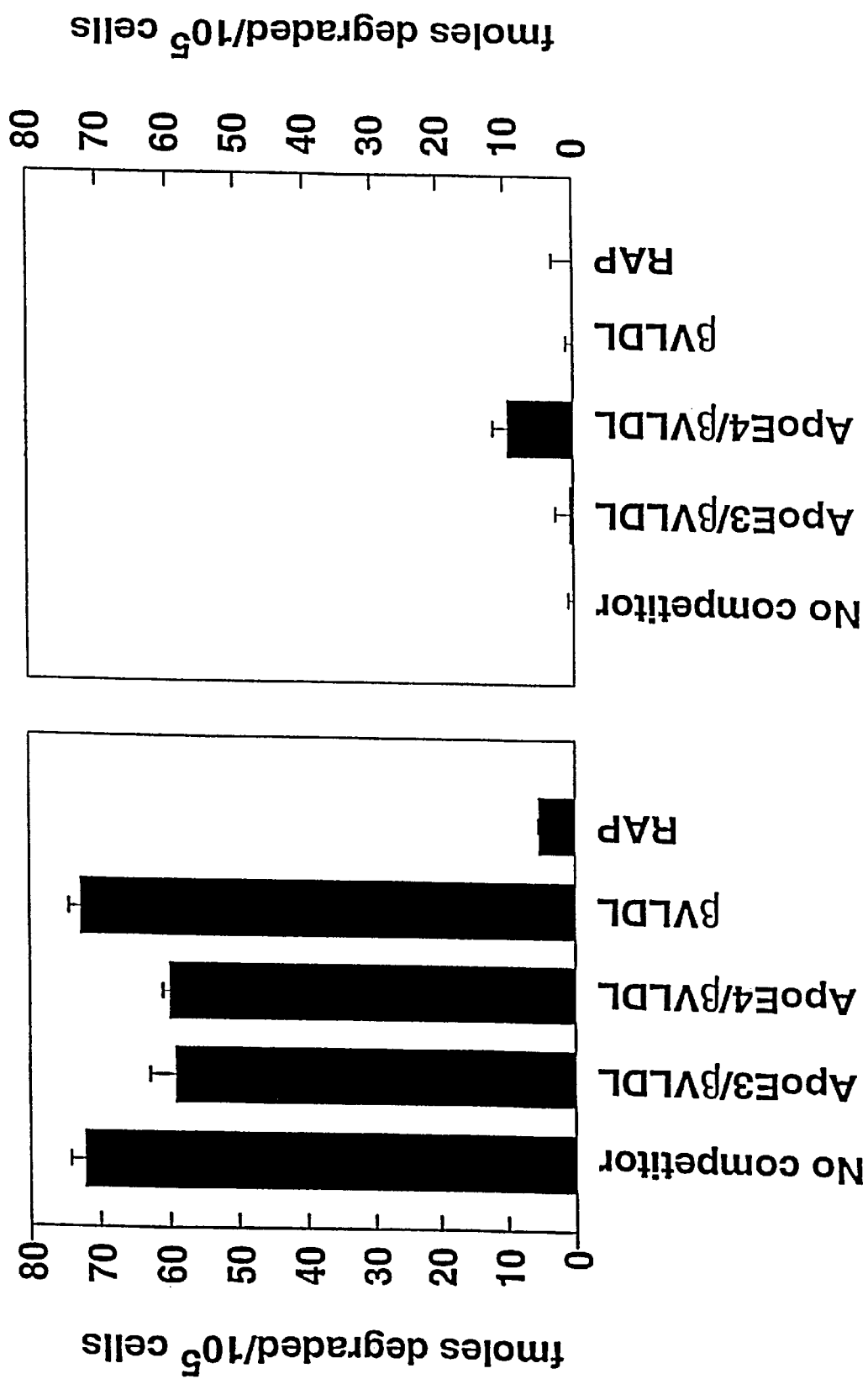
FIGS. 7A–B show a slight inhibition of APP degradation in LRP-containing fibroblasts by competition with apolipoprotein E3/β very low density lipoprotein or apolipoprotein E4/β very low density lipoprotein (panel A) as compared to the same competition in LRP-deficient fibroblasts.

As used herein, the LDL-receptor family is defined as those proteins which are recognized in the art as being formed from four structurally-related cell surface receptors and which mediate the endocytosis of lipoproteins and other plasma proteins (Brown et al., *Curr. Opin. Lipidology* 2:65–72 (1991)). These receptors share the following common features: cysteine-rich repeats which are responsible for ligand binding; cysteine-rich repeats of the epidermal growth factor-type (EGF-type); tyrosine-tryptophan-threonine-aspartate repeats; a single region spanning the membrane; and at least one internalizing signal (Willnow et al., *J. Biol. Chem.* 267:26172–21180 (1992)).

As used herein, an agent is said to reduce the amount or rate of binding if the amount or rate of binding is less in the presence of the agent than when the agent is absent. Under conditions when the amount or rate of reduction is nearly complete, there will be an actual inhibition or total blocking of binding.

As used herein, the agents of the present invention, ie. the Group I agents and the Group II agents, may be any composition of matter provided that it has the ability to bind to the APP-binding site on LRP (Group I) and/or the ability to bind to the LRP-binding site on APP (Group II). Suitable agents exhibiting these properties include, but are not limited to, peptides, antibodies, carbohydrates, nucleic acids, vitamins, pharmaceutical agents, and the like, including derivatives thereof.

The agents of the present invention may be identified and/or prepared according to any of the methods and techniques known to those skilled in the art. These agents, particularly peptide agents and antibody agents, may occur or be produced as monomer, dimers, triners, tetrameres or multimers. Such multimers can be prepared using enzymatic or chemical treatment of the native receptor molecules or be prepared using recombinant techniques. Preferably, the agents of the present invention are selected and screened at random or rationally selected or designed using protein modeling techniques.

For random screening, candidate agents are selected at random and assayed for their ability to reduce the amount or rate of binding of the amyloid β-precursor protein (APP) to the LDL receptor-related protein (LRP). Any of the suitable methods and techniques known to those skilled in the art may be employed to assay candidate agents.

For rational selection or design, the agent is selected based on the configuration of the LRP binding site found on APP or the APP binding site found on the LRP. Any of the suitable methods and techniques known to those skilled in the art may be employed for rational selection or design. For example, one skilled in the art can readily adapt currently available procedures to generate antibodies, peptides, pharmaceutical agents and the like capable of binding to a specific peptide sequence of LRP or APP. Illustrative examples of such available procedures are described, for example, in Hurby et al., "Application of Synthetic Peptides: Antisense Peptides," in *Synthetic Peptides, A User's Guide*, W. H. Freeman, N.Y., pp. 289–307 (1992); Kaspczak et al., *Biochemistry* 28:9230 (1989); and Harlow, *Antibodies*, Cold Spring Harbor Press, N.Y. (1990).

The agents of the present invention can alternatively be identified using modification of methods known in the art. For example, suitable peptide agents may be identified using the filter binding assay described by Mischak et al. (Mischak et al., *J. Gen. Virol.* 69:2653–2656 (1988) and Mischak et al., *Virology* 163:19–25 (1988)), wherein the peptide is applied to a suitable membrane, such as nitrocellulose, and the membrane is saturated with a detergent mixture in order to block any non-specific binding. The treated membrane is then incubated with labeled rhinovirus, e.g. with HRV2 labeled with $^{35}$S-methionine, in order to check the specific binding. After washing and drying of the membrane, specific binding can be visualized by autoradiography.

As noted above, the Group I agents of the present invention include those agents which bind directly to the APP binding site found on the LRP. Additionally, the Group I agents of the present invention bind to the LRP in interfering proximity with the APP binding site or bind to the LRP in such a manner so as to conformationally alter the APP binding site. Suitable Group I agents can therefore be first identified by their ability to bind the LRP and then by their ability to reduce the amount or rate at which APP binds to LRP. Illustrative examples of Group I agents of the present invention include, but are not limited to: soluble fragments of APP containing the KPI domain; anti-LRP antibodies; soluble fragments of receptor associated protein (RAP); $\alpha_2$-macroglobulin:proteinase complexes; pregnancy zone protein (PZP):proteinase complexes; tissue-type plasminogen activator; pro-urokinase-type plasminogen activator; tissue factor pathway inhibitor; apolipoprotein E-enriched lipoproteins; lipoprotein lipase; hepatic lipase; thrombospondin; and lactoferrin.

Preferred Group I agents are based on and derived from the amino acid sequence of the receptor associated protein (RAP). An especially preferred type of Group I agent is isolated RAP or a fragment thereof, such as a soluble fragment of RAP which contains the LRP binding site. Such agents act as competitive inhibitors of APP binding to its receptor in vitro as well as in vivo.

The preferred fragments of RAP are soluble under physiological conditions. The C-terminus of these polypeptides can be shortened as desired, provided that the binding capacity for the LRP particle remains intact. The preferred amino acid sequence of RAP corresponds to the human protein. Suitable RAP sequences can also be derived from the amino acid sequence of RAP isolated from other mammals or amphibia.

RAP, or a fragment thereof, may be produced using any of the methods and techniques known to those skilled in the art. For example, RAP can be purified from a source which naturally expresses the protein, can be isolated from a recombinant host which has been altered to express RAP or fragment thereof, or can be synthesized using protein synthesis techniques known in the art. The skilled artisan can readily adapt a variety of techniques in order to obtain Group I peptide agents which contain the LRP binding site found on RAP.

The isolation of native RAP proteins is known, as described, for example, in Ashcom et al., *J. Cell. Biol.* 110:1041–1048 (1990) and Jensen et al., *FEBS Lett.* 255:275–280 (1989). In order to generate fragments of RAP which contains the LRP binding site, isolated native protein may be converted by enzymatic and/or chemical cleavage to generate fragments of the whole protein, for example by reacting cell lines which express an RAP with an enzyme such as papain or trypsin or a chemical such as cyanogen bromide. Proteolytically active enzymes or chemicals are preferably selected in order to release the extracellular receptor region. Fragments which contain the LRP binding site, especially fragments which are soluble under physiological conditions, can then be isolated using known methods.

Alternatively, RAP or a fragment of RAP may be expressed in a recombinant bacteria, as described, for example, in Williams et al., *J. Biol. Chem.* 267:9035–9040 (1992) and Wurshawsky et al., J. Biol. Chem. 269:3325–3330 (1994).

The Group II agents of the present invention include compositions which bind to the LRP binding site found on APP. Additionally, the Group II agents of the present invention include compositions that bind to APP in interfering proximity to the LRP binding site. Suitable Group II agents can therefore be first identified by their ability to bind to APP and then by their ability to reduce the amount or rate at which APP binds to LRP. Illustrative examples of the Group II agents of the present invention include, but are not limited to, antibodies which bind to the LRP binding site found on APP and soluble fragments of LRP.

Preferred Group II agents include antibodies and antibody fragments which are capable of binding to a residue found on APP and consequently act as a competitive inhibitor for LRP binding. The most preferred antibodies or antibody fragments of the present invention bind to an LRP-specific epitope in APP. Antibodies, or other Group II agents such as anti-sense peptides, which bind to epitopes within this sequence reduce the amount or rate of APP binding to LRP.

The antibodies of the present invention include polyclonal and monoclonal antibodies, as well as antibody fragments and derivatives that contain the relevant antigen binding domain of the antibodies. Such antibodies or antibody fragments are preferably used in the diagnostic and therapeutic embodiments of the present invention.

Suitable monoclonal and polyclonal antibodies may be prepared by any of the methods and techniques well known in the art, such as described in, for example, A. M. Campbell, *Monoclonal Antibody Technology: Laboratory Techniques in Biochemistry and Molecular Biology*, Elsevier Science Publishers, Amsterdam, The Netherlands (1984) and Harlow; *Antibodies,* Cold Spring Harbor Press, N.Y. (1989). For example, an antibody capable of binding to a domain of APP can be generated by immunizing an animal with a polypeptide whose sequence is encoded by that domain. Any animal (mouse, rabbit, etc.) which is known to produce antibodies can be utilized to produce antibodies with the desired specificity and suitable methods for immunization of these animals are well known in the art, including, for example, subcutaneous or intraperitoneal injection of the polypeptide. One skilled in the art will recognize that the amount of polypeptide used for immunization will vary based on a number of factors, including the animal which is immunized, the antigenicity of the polypeptide selected, and the site of injection.

The polypeptides used as an immunogen may be modified as appropriate or administered in an adjuvant in order to increase the peptide antigenicity. Suitable methods increasing antigenicity are well known in the art, and include, for example, coupling the antigen with a heterologous protein (such as globulin or β-galactosidase) or through the inclusion of an adjuvant during immunization.

A preferred method of generating monoclonal antibodies comprises removing spleen cells from the immunized animals, fusing these cells with myeloma cells, such as SP2/0-Ag14 myeloma cells, and allowing them to become monoclonal antibody-producing hybridoma cells. Any one of a number of methods well known in the art may be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988); Kishimoto et al., *Proc. Natl. Acad. Sci USA* 87:2244–2248 (1990)). Hybridomas secreting the desired antibodies are cloned and the class and subclass of the secreted antibodies are determined using procedures known in the art (Campbell, A. M., *Monoclonal Antibody Technology: Laboratory Techniques in Biochemistry and Molecular Biology,* Elsevier Science Publishers, Amsterdam, The Netherlands (1984)).

For polyclonal antibodies, antibody-containing antisera is preferably isolated from the immunized animal and is screened for the presence of antibodies with the desired specificity using one of the above-described procedures.

The present invention further provides hybrid cell lines which secrete monoclonal antibodies selective for the peptide agents of Group I and/or Group II. These monoclonal antibodies are capable of wholly or partially neutrlizing the activity of the polypeptides or specifically binding to one of the said polypeptides. These monoclonal antibodies can be used for qualitative and/or quantitative measurement or for purification of the polypeptides according to the invention. The present invention therefore also includes test systems which contain the monoclonal antibodies herein described.

Antibodies may be used as an isolated whole antibody, or can be used as a source for generating antibody fragments which contain the antigen binding site of the antibody. Examples of such antibody fragments include, but are not limited to the $F_v$, the F(ab), the F(ab)$_2$, fragment, as well as single chain antibodies.

Various methods known in the art can be used to generate such fragments without undue experimentation. Recombinant techniques are preferred for generating large quantities of antibodies, antibody fragments and single chain antibodies, as described, for example, in Pluckthum, *Bio/Technology* 10:163–167 (1992); Carter et al., *Bio/Technology* 10:167–170 (1992); and Mullinax et al., *Biotechniques* 12:864–869 (1992). In addition, recombinant techniques may be used to generate heterobifunctional antibodies.

In general, recombinant production of antibodies, antibody fragments or derivatives thereof, uses MRNA encoding an antibody which is isolated from hybridoma cells that produce the desired antibody. This mRNA is then used as a source for generating a cDNA molecule which encodes the antibody, or a fragment thereof. Once obtained, the cDNA may be amplified and expressed according to known methods in a variety of eukaryotic and prokaryotic hosts.

The present invention further includes derivatives of antibodies (antibody derivatives). As used herein, an "antibody derivatives" contain an antibody of the present invention, or a fragment thereof, as well as an additional moiety which is not normally a part of the antibody. Such moieties may improve the solubility, absorption, biological half-life, etc., of the antibody, decrease the toxicity of the antibody, eliminate or attenuate any undesirable side effect of the antibody, or serve as a detectable marker of the presence of the antibody. Moieties capable of mediating such effects are well known in the art.

Detectably labeled antibodies constitute a special class of the antibody derivatives of the present invention. An antibody is said to be "detectably labeled" if the antibody, or fragment thereof, is attached to a molecule which is capable of identification, visualization, or localization using known methods. Suitable detectable labels include radioisotopic labels, enzyme labels, non-radioactive isotopic labels, fluorescent labels, toxin labels, affinity labels, chemiluminescent labels and nuclear magnetic resonance contrast agents.

Illustrative examples of suitable enzyme labels include, but are not limited to, malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include, but are not limited to, $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl. Med* 10:296–301 (1985); Carasquillo et al., *J. Nucl. Med.* 28:281–287 (1987)). For example, $^{111}$In coupled to monoclonal antibodies with 1-(p-isothiocyanatobenzyl)-DPTA has shown little uptake in non-tumorous tissues, particularly the liver, and therefore enhances specificity of tumor localization (Esteban et al., *J. Nucl. Med.* 28:861–870 (1987)).

Illustrative examples of suitable non-radioactive isotopic labels include, but are not limited to, $^{157}$Gd, $^{55}$Mn, $^{162}$Dy, $^{52}$Tr, and $^{56}$Fe.

Illustrative examples of suitable fluorescent labels include, but are not limited to, an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Illustrative examples of suitable toxin labels include diphtheria toxin, ricin, and cholera toxin.

Illustrative examples of chemiluminescent labels include a luminal label, an isoluminal label, an aromatic acridinium ester label, an imidazole label, an acridinium salt label, an oxalate ester label, a luciferin label, a luciferase label, and an aequorin label.

Illustrative examples of nuclear magnetic resonance contrasting agents include paramagnetic heavy metal nuclei such as Gd, Mn, and Fe.

Typical techniques for binding the above-described labels to antibodies are provided by Kennedy et al. (*Clin. Chim. Acta* 70:1–31 (1976)), and Schurs et al (*Clin. Chim. Acta* 81:1–40 (1977)), which are both herein incorporated in their entirety by reference. Coupling techniques mentioned in the latter reference include the glutaraldehyde method, the periodate method, the dimaleimide method, and the m-maleimidobenzyl-N-hydroxy-succinimide ester method.

The present invention additionally includes humanized forms of these antibodies. Humanized forms of the antibodies may be produced, for example, by replacing an immunogenic portion of an antibody with a corresponding, non-immunogenic portion (chimeric antibodies) (Better, et al., *Science* 240:1041–1043 (1988)). Alternatively, suitable "humanized" antibodies can be produced by CDR or CEA grafting/substitution as described, for example, in Jones, et al., *Nature* 321:552–525 (1986); Verhoeyan et al., *Science* 239:1534 (1988); and Beidler, et al., *J. Immunol.* 141:4053–4060 (1988).

Another type of the Group II agents of the present invention are peptide agents which are classified as antisense-peptide sequences. Antisense-peptide sequences are short peptides which are specifically designed to bind to a particular amino acid sequence. In general, such antisense peptide agents may be generated using methods known in the art, such as those described, for example, in Hurby et al., "Application of Synthetic Peptides: Antisense Peptides," in *Synthetic Peptides, A User's Guide*, W. H. Freeman, N.Y., pp. 289–307 (1992) and Kaspczak et al., *Biochemistry* 28:9230–8 (1989).

An additional class of the Group II agents of the invention are natural ligands of APP. As used herein, a natural ligand of APP is defined as any substance which binds to APP, such as soluble fragments of LRP containing the APP binding site. Such soluble fragments may be prepared by any suitable method known to those skilled in the art, such as the method of Davis et al., *Nature* 326:760–765 (1987), which involves deletion of the entire EGF domain. Moreover, soluble forms of the receptor may be formed by inserting a stop codon in front of the region of DNA encoding the cytoplasmic or transmembrane domain (Yokade et al., *J. Cell. Biol.* 117:39 (1992)).

The agents of the present invention may be used in vitro and/or in vivo to study LRP attachment and to reduce the rate of onset and/or ameliorate the duration and severity of Alzheimer's disease. In addition, the agents of the present invention may be used in qualitative, quantitative and preparative assays and purification procedures to isolate, identify and facilitate the purification of APP.

For in vivo use, the agents of the present invention may be provided to a patient as a means of reducing the amount or rate of APP binding to LRP (Hayden, et al., *Antiviral Res.* 9:233–247 (1988)).

The present invention therefore provides pharmaceutical compositions comprising a Group I agent and or a Group II agent. These pharmaceutical compositions may be administered orally, rectally, parenterally, intracistemally, intravaginally, intraperitoneally, topically (as by powders, ointments, drops or transdermal patch), bucally, or as an oral or nasal spray. As used herein, "pharmaceutically acceptable carrier" is intended to mean a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion. One of ordinary skill will recognize that the choice of a particular mode of administration can be made empirically based upon considerations such as the particular disease state being treated; the type and degree of the response to be achieved; the specific agent or composition employed; the age, body weight, general health, sex and diet of the patient; the time of administration and rate of excretion of the agent or composition; the duration of the treatment; drugs (such as a chemotherapeutic agent) used in combination or coincidental with the specific composition; and like factors well known in the medical arts.

Pharmaceutical compositions of the present invention for parenteral injection may comprise pharmaceutically acceptable sterile aqueous or nonaqueous solutions, dispersions, suspensions or emulsions as well as sterile powders for reconstitution into sterile injectable solutions or dispersions just prior to use. Illustrative examples of suitable aqueous and nonaqueous carriers, diluents, solvents or vehicles include, but are not limited to, water, ethanol, polyols (such as glycerol, propylene glycol, polyethylene glycol, and the like), carboxymethylceuulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the therapeutic agent or inhibitor, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or rnicroemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are preferably mixed with at least one pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and I) lubricants such as talc, calcium stearate, magnesium stearate, solid polyethylene glycols, sodium lauryl sulfate, and mixtures thereof. In the case of capsules, tablets and pills, the dosage form may also comprise buffering agents as appropriate.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Illustrative examples of embedding compositions which can be used include polymeric substances and waxes.

The active agents of Group I and/or Group II can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions may also contain adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The agent or inhibitor can also be administered in the form of liposomes. As is known to those skilled in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the agent or inhibitor, stabilizers, preservatives, excipients, and the like. Preferred lipids are phospholipids and phosphatidyl cholines (lecithins), both natural and synthetic. Methods to form liposomes are known in the art. See, e.g., Prescott, ed., METHODS IN CELL BIOLOGY, Volume XIV, Academic Press, New York, N.Y. (1976), p. 33 et seq.

The agents of the present invention can be formulated according to known methods to prepare pharmaceutically acceptable compositions, whereby these materials, or their functional derivatives, are combined in a mixture with a pharmaceutically acceptable carrier vehicle. Suitable vehicles and their formulation, inclusive of other human proteins, e.g., human serum albumin, are well known in the art. In order to form a pharmaceutically acceptable composition suitable for effective administration, such compositions will contain an effective amount of one or more agents of the present invention.

Additional pharmaceutical methods may be employed to control the duration of action. Control release preparations may be achieved through the use of polymers to complex or absorb the therapeutic agents of the invention. The controlled delivery may be exercised by selecting appropriate macromolecules (such as polyesters, polyamino acids, polyvinyl, pyrrolidone, ethylenevinylacetate, methylcellulose, carboxymethylcellulose, or protamine sulfate) and methods of incorporation in order to control release. Another possible method to control the duration of action by controlled release preparations is to incorporate antibodies into particles of a polymeric material such as polyesters, polyamino acids, hydrogels, poly(lactic acid) or ethylene vinyl acetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions.

The pharmaceutical formulations of the present invention are prepared, for example, by admixing the active agent with solvents and/or carriers, optionally using emulsifiers and/or dispersants, whilst if water is used as the diluent, organic solvents may be used as solubilizing agents or auxiliary solvents. As described above, the excipients used include, for example, water, pharmaceutically acceptable organic solvents such as paraffins, vegetable oils, mono- or poly-functional alcohols, carriers such as natural mineral powders, synthetic mineral powders, sugars, emulsifiers and lubricants.

One of ordinary skill will appreciate that effective amounts of the inventive therapeutic agents can be determined empirically and may be employed in pure form or, where such forms exist, in pharmaceutically acceptable salt, ester or prodrug form. The agonist or antagonist my be administered in compositions in combination with one or more pharmaceutically acceptable excipients. It will be understood that, when administered to a human patient, the total daily usage of the agents and compositions of the present invention will be decided by the attending physician within the scope of sound medical judgement. The specific therapeutically effective dose level for any particular patient will depend upon a variety of factors including the type and degree of the response to be achieved; the specific agent or composition employed; the age, body weight, general health, sex and diet of the patient; the time of administration, route of administration, and rate of excretion of the agent or composition; the duration of the treatment; drugs (such as a chemotherapeutic agent) used in combination or coincidental with the specific composition; and like factors well known in the medical arts.

Techniques of dosage determination are well known in the art for antibody and peptide agents. In general, it is desirable to provide a patient with a dosage of antibody or peptide agent in the range of from about 1 pg/kg to 10 mg/kg (body weight of patient). The therapeutically effective dose can be lowered if the agent of the present invention is additionally administered with another compound. As used herein, one compound is said to be additionally administered with a second compound when the administration of the two compounds is in such proximity of time that both compounds can be detected at the same time in the patient's serum.

For example, satisfactory results are obtained by oral administration of therapeutic dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging may also be arranged in a patient specific manner to provide a predetermined concentration of an agent in the blood, as determined by the RIA technique. Thus patient dosaging may be adjusted to achieve regular on-going trough blood levels, as measured by RIA, on the order of from 50 to 1000 ng/ml, preferably 150 to 500 ng/hml.

The agents of the present invention are intended to be provided to a patient in an amount sufficient to reduce the amount or rate of binding of human APP to LRP. An amount is said to be sufficient to "reduce the amount or rate of APP binding" if the dosage, route of administration, etc. of the agent is sufficient to reduce the amount or rate of APP attachment to the LRP receptor. Such an effect can be assayed, for example, by examining the onset of Alzheimer's disease symptoms occurring in vivo, or by correlating in vitro blocking studies with predicted in vivo efficacy.

The administration of the agents of the present invention may be for either prophylactic or therapeutic purpose. When provided prophylactically, the agent is provided in advance of any Alzheimer's disease symptoms. The prophylactic administration of the agent serves to prevent or reduce the rate of onset of symptoms. When provided therapeutically, the agent is provided at (or shortly after) the onset of the appearance of symptoms of actual disease. The therapeutic administration of the agent serves to reduce the severity and duration of Alzheimer's disease.

The present invention further includes the use of the agents of the present invention in diagnostic applications. The Group I agents of the present invention can be used to detect the presence of LRP in a test sample. The Group II agents of the present invention can be used to detect the presence of APP in a test sample.

Conditions for incubating an agent with a test sample vary. Incubation conditions will depend on factors such as the type of agent, format, and detection system employed for the assay, as well as the nature of the test sample used in the assay. For example, condition will vary slightly when a whole antibody, a single chain antibody, a F(ab) fragment, or a peptide agent is used. One skilled in the art will recognize that any one of the commonly available immunological assay formats (such as radioimmunoassays, enzyme-linked immunosorbent assays, diffusion based ouchterlony, or rocket immunofluorescent assays) can readily be adapted to employ the antibodies of the present invention. Examples of such assays can be found in T. Chard, *An Introduction to Radioimmunoassay and Related Techniques,* Elsevier Science Publishers, Amsterdam, The Netherlands (1986); G. R. Bullock et al., *Techniques in Immunocytochemistry,* Academic Press, Orlando, Fla. Vol. 1 (1982), Vol. 2 (1983), Vol. 3 (1985); and P. Tijssen, P., *Practice and Theory of Enzyme Immunoassays: Laboratory Techniques in Biochemistry and Molecular Biology,* Elsevier Science Publishers, Amsterdam, The Netherlands (1985).

In one embodiment of the above-described method, the agent of the present invention is immobilized on a solid support for use in the diagnostic assay. Illustrative examples of such solid supports include, but are not limited to, plastics such as polycarbonate, complex carbohydrates such as agarose and sepharose, and acrylic resins, such as polyacrylamide and latex beads. Techniques for coupling agents such as antibodies, peptides and the like to such solid supports are well known in the art, as described, for example, in D. M. Weir et al., *Handbook of Experimental Immunology,* 4th Ed., Blackwell Scientific Publications, Oxford, England, Chapter 10 (1986) and W. D. Jacoby et al., *Meth. Enzym.* 34, Academic Press, N.Y. (1974).

Additionally, one or more of the agents of the present invention which is used in one of the above-described methods can be detectably labelled prior to use, for example, through the use of radioisotopes, affinity labels (such as biotin, avidin, etc.), enzymatic labels (such as horse radish peroxidase, alkaline phosphatase, etc.) fluorescent labels (such as FITC or rhodamine, etc.), paramagnetic atoms, etc. Procedures for accomplishing such labelling are well-known in the art (L. A. Sternberger et al., *J. Histochem. Cytochem.* 18:315 (1970); E. A. Bayer et al., *Meth. Enzym.* 62:308 (1979); E. Engval et al., *Immunol.* 109:129 (1972); and J. W. Goding, *J. Immunol. Meth.* 13:215 (1976)).

The materials used in the inventive assays are ideally suited for the preparation of a kit. For example, the present invention provides a compartmentalized kit to receive in close confinement, one or more containers which comprises:

a) a first container comprising an agent capable of binding to the LRP binding site; and
b) one or more other containers comprising one or more of the following: wash reagents and reagents capable of detecting the presence of bound agents from the first container.

As used herein, a compartmentalized kit includes any kit in which reagents are contained in separate containers. Illustrative examples of such containers include, but are not limited to, small glass containers, plastic containers or strips of plastic or paper. Particularly preferred types of containers allow the skilled worker to efficiently transfer reagents from one compartment to another compartment such that the samples and reagents are not cross-contaminated and the agents or solutions of each container can be added in a quantitative fashion from one compartment to another. Such containers include, but are not be limited to, a container which will accept the test sample, a container which contains one or more of the agents of the present invention used in the assay, containers which contain wash reagents (such as phosphate buffered saline, Tris-buffers, etc.), and containers which contain the reagents used to detect the bound agent.

The types of detection reagents which can be used in the above described kits include, but are not limited to, labelled secondary agents, or in the alternative, if the primary agent is labelled, enzymatic or agent binding reagents which are capable of reacting with the labelled agent. One skilled in the art will readily recognize that the agents of the present invention can be readily incorporated into one of the established kit formats which are well known in the art.

A further aspect of the present invention concerns DNA molecules which encode for the polypeptide and antibody agents of Group I and/or Group II. The starting nucleotide molecules can be obtained by the person skilled in the art using known methods. Moreover, the DNA molecules, where the amino acid sequence is known, may be produced synthetically (e.g. according to Edge et al., *Nature* 292:756–762 (1981)) or by methods such as PCR (Sambrook et al., *Molecular Cloning: A Laboratory Manual,* Cold Spring Harbor Laboratory Press (1989)). The DNA sequences of the present invention include not only the actual nucleotide sequence used by the organism from which the receptor protein is derived but also includes all degenerate forms which encode a peptide with the desired sequence.

The invention includes DNA sequences which have been modified utilizing methods known in the art, such as those generated by mutation, deletion, transposition or addition. The preferred mutations will introduce stop codons within the RAP sequence so that a truncated protein will be generated.

The present invention further includes DNA vectors which contain the DNA sequences described above and below. In particular, these may be vectors in which the DNA molecules described are functionally linked to control sequences which allows expression of the corresponding polypeptides. These are preferably plasmids which can be replicated and/or expressed in prokaryotes such as *E. coli* and/or in eukaryotic systems such as yeasts or mammalian cell lines. These vectors may also be mammalian viral vectors which can be replicated and/or expressed in eukaryotes such as mammalian cell lines and in the human patient, as "host," for integration into the cellular genome of the patient and expression as genetic therapy systems.

The invention also includes host organisms transformed with the above vectors. Expression in prokaryotes and eukaryotes may be carried out using techniques known in the art. The DNA sequences according to the invention may be expressed as fusion polypeptides or as intact, native polypeptides. Fusion proteins may advantageously be produced in large quantities. They are generally more stable than the native polypeptide and are easy to purify. The expression of these fusion proteins can be controlled by normal host DNA sequences.

For example, the DNA sequences according to the invention can be cloned and expressed as lacZ fusion genes in *E.* coli. A person skilled in the art has a variety of vector systems available for this purpose, e.g. the pUR-vector series (U. Rüther and B. Müller-Hill, EMBO J. 2:1791 (1983)). The bacteriophage promoter $\lambda p_R$ may also be used, in the form of the vectors pEX-1 to –3, for expressing large amounts of Cro-β-galactosidase fusion protein (K. K. Stanley and J. P. Luzio, EMBO J. 3:1429 (1984)). Analogously, the tac promoter which can be induced with IPTG can also be used, for example in the form of the pROK-vector series (CLONTECH Laboratories).

The prerequisite for producing intact native polypeptides using E. coli is the use of a strong, regulatable promoter and an effective ribosome binding site. Promoters which may be used for this purpose include the temperature sensitive bacteriophage $\lambda p_L$-promoter, the tac-promoter inducible with IPTG or the T7-promoter. Numerous plasmids with suitable promoter structures and efficient ribosome binding sites have been described, such as for example pKC30 ($\lambda p_L$; Shimatake and Rosenberg, Nature 292:128 (1981), pKK173-3 (tac, Amann and Brosius, Gene 40:183 (1985)) or pET-3 (T7-promoter (Studier and Moffat, J. Mol. Biol. 189:113 (1986)).

A number of other suitable vector systems for expressing the DNA according to the invention in E. coli are known from the prior art and are described, for example, in Sambrook et al., Molecular Cloning: A Laboratory Manual, Cold Spring Harbor Laboratory Press (1989)).

Suitable E. coli strains which are specifically tailored to a particular expression vector are known to those skilled in the art (Sambrook et al., Molecular Cloning: A Laboratory Manual, Cold Spring Harbor Laboratory Press (1989)). The experimental performance of the cloning experiments, the expression of the polypeptides in E. coli and the working up and purification of the polypeptides are known and are described, for example, in Sambrook et al., Molecular Cloning: A Laboratory Manual, Cold Spring Harbor Laboratory Press (1989). In addition to prokaryotes, eukaryotic microorganisms such as yeast may also be used.

For expression in yeast, the plasmid YRp7 (Stinchcomb et al. Nature 282:39 (1979); Kingsman et al., Gene 7:141 (1979); Tschumper et al., Gene 10:157 (1980)) and the plasmid YEp13 (Bwach et al., Gene 8:121–133 (1979)) are used, for example. The plasmid YRp7 contains the TRP1-gene which provides a selection marker for a yeast mutant (e.g ATCC No. 44076) which is incapable of growing in tryptophan-free medium. The presence of the TRP1 defect as a characteristic of the yeast strain used then constitutes an effective aid to detecting transformation when cultivation is carried out without tryptophan. The same is true with the plasmid YEp13, which contains the yeast gene LEU-2, which can be used to complete a LEU-2-minus mutant.

Other suitable marker genes for yeast include, for example, the URA3- and HIS3-gene. Preferably, yeast hybrid vectors also contain a replication start and a marker gene for a bacterial host, particularly E. coli, so that the construction and cloning of the hybrid vectors and their precursors can be carried out in a bacterial host. Other expression control sequences suitable for expression in yeast include, for example, those of PHO3- or PHO5-gene.

Other suitable promoter sequences for yeast vectors contain the 5'-flanking region of the genes of ADH I (Ammerer, Methods of Enzymology 101:192–210 (1983)), 3-phosphoglycerate kinase (Hitzeman et al., J Biol. Chem. 255:2073 (1980)) or other glycolytic enzymes (Kawaski and Fraenkel, BBRC 108:1107–1112 (1982)) such as enolase, glyceraldehyde-3-phosphate-dehydrogenase, hexokinase, pyruvate-decarboxylase, phosphofructokinase, glucose-6-phosphate isomerase, phosphoglucose-isomerase and glucokinase. When constructing suitable expression plasmids, the termination sequences associated with these genes may also be inserted in the expression vector at the 3'-end of the sequence to be expressed, in order to enable polyadenylation and termination of the MRNA.

Other promoters are the promoter regions of the genes for alcohol dehydrogenase-2, isocytochrome C, acid phosphatase and enzymes which are responsible for the metabolism of maltose and galactose. Promoters which are regulated by the yeast mating type locus, such as promoters of the genes BARI, MFα1, STE2, STE3, STE5 can be inserted in temperature regulated systems by the use of temperature-dependent sir mutations. (Rhine, Ph.D. Thesis, University of Oregon, Eugene, Oreg. (1979); Herskowitz and Oshima, The Molecular Biology of the Yeast Saccharomyces, Cold Spring Harbor Laboratory Press, part I, pp. 181–209 (1981)). Generally, however, any vector which contains a yeast-compatible promoter and origin replication and termination sequences is suitable. Thus, hybrid vectors which contain sequences homologous to the yeast $2\mu$ plasmid DNA may also be used. Such hybrid vectors are incorporated by recombination within the cells of existing $2\mu$-plasmids or replicate autonomously.

In addition to yeasts, other eukaryotic systems may, of course, be used to express the polypeptides according to the invention. Since post-translational modifications such as disulphide bridge formation, glycosylation, phosphorylation and/or oligomerization are frequently necessary for the expression of biologically active eukaryotic proteins by means of recombinant DNA, it may be desirable to express the DNA according to the invention not only in mammalian cell lines but also insect cell lines.

Functional prerequisites of the corresponding vector systems comprise, in particular, suitable promoter, termination and polyadenylation signals as well as elements which make it possible to carry out replication and selection in mammalian cell lines. For expression of the DNA molecules according to the invention it is particularly desirable to use vectors which are replicable both in mammalian cells and also in prokaryotes such as E. coli.

Vectors derived from viral systems such as SV40, Epstein-Barr-virus, etc., include, for example, pTK2, pSV2-dhfv, pRSV-neo, pKO-neo, pHyg, p205, pHEBo, etc. (Sambrook et al., Molecular Cloning: A Laboratory Manual, Cold Spring Harbor Press, N.Y. (1989)).

After transformation in suitable host cells, e.g. CHO-cells, corresponding transformed cells may be obtained with the aid of selectable markers (thymidine-kinase, dihydrofolate-reductase etc.) and the corresponding polypeptides are isolated after expression. The host cells suitable for the vectors are known, as are the techniques for transformation (microinjection, electroporation, calcium phosphate method, etc.) as described, for example, in Sambrook et al., Molecular Cloning: A Laboratory Manual, Cold Spring Harbor Press, N.Y. (1989).

For cloning corresponding DNA fragments in prokaryotic or eukaryotic systems, the selected vector may cut, for example, with a restriction endonuclease and, optionally after modification of the linearized vector thus formed, an expression control sequence equipped with corresponding restriction ends is inserted. At the 3'-end (in the direction of translation) the expression control sequence contains the recognition sequence of a restriction endonuclease, so that the vector already containing the expression control sequence is digested with the said restriction enzyme and the DNA molecule according to the invention, provided with ends which fit, can be inserted. It is advantageous to cleave the vector which already contains the expression control sequence with a second restriction endonuclease inside the vector DNA and to insert the DNA molecule provided with the correct ends into the vector fragment produced. The techniques required are described, for example, by Sambrook et al. *Molecular Cloning: A Laboratory Manual* Cold Spring Harbor Press. N.Y. (1989).

Apart from the DNA molecules specified, the invention also relates to processes for preparing the vectors described herein, particularly expression vectors. These vectors are characterized in that a DNA provided with corresponding ends and coding for a functional derivative or a fragment of the LRP receptor is inserted into a vector DNA cut with restriction endonucleases and containing the expression control sequences described by way of example, in such a way that the expression control sequences regulate the expression of the DNA inserted. The peptides and antibody agents of the present invention which are obtained by the expression of recombinant DNA or from the native receptor molecule may, of course, also be derivatized by chemical or enzymatic processes.

The present invention is described in further detail in the following non-limiting examples.

EXAMPLE 1

$^{125}$I-labeled APP$_s$770 Degradation by LRP-expressing Fibroblasts

Wells containing 2×10$^5$ LRP-expressing (MEF) or LRP-deficient (PEA13) cells were incubated with various concentrations (0.37–10 nM) of $^{125}$I-APPs770 (Panels A and B) or 125I-APPs695 (Panels C and D) for 10 h at 37° C. in the absence of competitor (●) or in the presence of either 1 μM RAP (○), or 100 μg/ml heparin (□). The cellular degradation of $^{125}$I-labeled APP$_s$770 by LRP-expressing MEF cells is shown in panel A and by LRP-deficient PEA13 cells in panel B. The cellular degradation of $^{125}$I-APP$_s$695 by LRP-expressing cells is depicted in panel C and by LRP-deficient cells in panel D. Plotted values represent means of duplicate determinations. Inset to panel B, autoradiogram of $^{125}$I-labeled APP$_s$770 (lane 1) and APP$_s$695 (lane 2). The migration position of molecular mass standards are indicated on the right in kDa.

EXAMPLE 2

LRP-deficient cells internalize and degrade $^{125}$I-LDL, but not $^{125}$I-α$_2$M Wells containing 2×10$^5$ LRP-expressing (●) or LRP-deficient (○) mouse fibroblasts were incubated with $^{125}$I-LDL (8 μg/ml) or $^{125}$I-α$_2$M* (1.4 nM) for selected time intervals. Specific internalization and degradation was determined by incubation of $^{125}$I-ligand in the presence of a 200-fold excess unlabeled ligand. Shown are the amounts of $^{125}$I-LDL internalized (panel A) and degraded (panel B), $^{125}$I-α$_2$M* internalized (panel C) and degraded (panel D). The plotted values represent means of duplicate determinations.

EXAMPLE 3

Time course of the cellular internalization and degradation of $^{125}$I-APP$_s$770

Mouse fibroblasts (2×10$^5$ cells per well) were incubated for selected times with $^{125}$I-APP$_s$770 (1 nM) in the absence of competitor (●) or in the presence of either 1 μM RAP (○), or 100 μg/ml heparin (□). The amount of radioactivity internalized and degraded was determined at the indicated time intervals. Shown is the amount of internalization and degradation of $^{125}$I- APP$_s$770 by LRP-expressing MEF cells (panels A and B, respectively) and the internalization and degradation of $^{125}$I-APP$_s$770 by LRP-deficient PEA13 cells (panels C and D, respectively). The plotted values are means of duplicate determinations.

EXAMPLE 4

LRP-antibodies inhibit the degradation of $^{125}$I-APP$_s$770 by mouse fibroblasts Mouse fibroblasts (2×10$^5$ cells/well) were incubated for 18 h at 37° C. with $^{125}$I-APP$_s$770 (10 nM) in the absence of competitor or in the presence of either heparin (100 μg/ml), chloroquine (0.1 mM), RAP (1 μM), affinity purified anti-LRP IgG (100 μg/ml), or control IgG against the cytoplasmic domain of LRP (100 μg/ml). Panels show the amount of $^{125}$I-APP$_s$770 degraded by mouse fibroblasts expressing LRP (A) or ones deficient in LRP expression (B). The data shown are means of duplicate determinations ÷S.E.

EXAMPLE 5

LRP binds directly to APP$_s$770 in ELISA

In panel A, zinc-coated wells (○) or zinc-coated wells incubated with APP$_s$770 (●) were incubated with the APP$_s$770 monoclonal antibody 7H5. In panel B, increasing concentrations of LRP (0.14–300 nM) were incubated for 18 h at 4° C. with zinc-coated wells (○) or zinc-coated wells with captured APP$_s$770 (●). Panel C, LRP (25 nM) was incubated with zinc-coated wells (○) or zinc-coated wells with captured APP$_s$770 (●) in the presence of increasing concentrations of RAP (0.2–450 nM). Bound receptor was detected with the monoclonal LRP antibody 8G1. In the absence of LRP there was no binding of 8G1 IgG to APP$_s$770-coated wells. Plotted values represent means of duplicate determinations.

EXAMPLE 6

$^{125}$I-APP$_s$770:Factor IXa complex is degraded by LRP-expressing cells but not by LRP-deficient cells Wells containing 2×10$^5$ LRP-expressing (MEF) or LRP-deficient (PEA13) cells were incubated with $^{125}$I-APP$_s$770 (5 nM) or $^{125}$I-APP$_s$770:FIXa (3 nM) for 18 h at 37° C. in the absence of competitor or in the presence of 1 μM RAP. The amount of $^{125}$I-labeled APP$_s$770 or $^{125}$I-APP$_s$770:Factor IXa degraded by LRP-expressing MEF cells is shown in panel A and that by LRP-deficient PEA13 cells in panel B. Plotted values represent means of duplicate determinations.

EXAMPLE 7

Effect of apoE isoforns on the degradation of $^{125}$I-APP$_s$770 by mouse fibroblasts Mouse fibroblasts (2×10$^5$) were incubated for 18 h at 37° C. with $^{125}$I-APP/PN-2 (8.8 nM) in the absence of competitor or in the presence of either RAP (1 μM)), 10 μg/ml apoE3/βVLDL, 10 μg/ml apoE4/βVLDL, or 10 μg/ml βVLDL. The concentration of apoE-enriched βVLDL represent the βVLDL protein before enrichment with apoE. Panels show the amount of $^{125}$I-APP$_s$770 degradation by mouse fibroblasts expressing LRP (A) or deficient in LRP expression (B). The data shown are means of duplicate determinations ±S.E. The inhibition was statistically significant for both apoE3-βVLDL and apoE4-βVLDL, and for RAP F(4,15)=21.65, P=0.0001; Fisher protected least significant difference post hoc test showed that both apoE3-βVLDL and apoE4-βVLDL were different from βVLDL alone (p<0.05 for both) but not from each other. RAP was also significantly different than all other categories (p<0.001).

It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

The disclosures of all patents, patent applications, and publications referred to above are hereby expressly incorporated herein by reference.

What is claimed is:

1. A method for reducing catabolism of extracellular secreted amyloid β-precursor protein which comprises contacting a mammalian cell with an agent that reduces the amount or rate of binding of amyloid β-precursor protein (APP) with the low density lipoprotein receptor-related protein.

2. The method according to claim 1, wherein said agent is an agent which binds to the amyloid β-precursor protein.

3. The method according to claim 1, wherein said agent is an agent that binds to the low density lipoprotein receptor-related protein.

4. The method according to claim 3, wherein said agent is an antibody or an antibody fragment containing the antigen binding domain that binds to amyloid β-precursor protein.

5. The method according to claim 3, wherein said agent is a functional derivative of low density receptor-related protein.

6. The method according to claim 1, wherein said contacting occurs in vitro.

* * * * *